US009855203B2

(12) United States Patent
McConaughy et al.

(10) Patent No.: US 9,855,203 B2
(45) Date of Patent: *Jan. 2, 2018

(54) PRESERVING PERSONAL CARE COMPOSITIONS

(71) Applicant: The Procter & Gamble Company, Cincinnati, OH (US)

(72) Inventors: Shawn David McConaughy, Cincinnati, OH (US); Valerie Lynn Vanlandingham, Richmond, IN (US); Scott Brian Bintrim, Carmel, IN (US); Adam Michael Pitz, Morrow, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/315,515

(22) Filed: Jun. 26, 2014

(65) Prior Publication Data

US 2015/0000059 A1 Jan. 1, 2015

Related U.S. Application Data

(60) Provisional application No. 61/886,502, filed on Oct. 3, 2013, provisional application No. 61/840,084, filed
(Continued)

(51) Int. Cl.
*A61K 8/46* (2006.01)
*A47K 7/03* (2006.01)
(Continued)

(52) U.S. Cl.
CPC ............... *A61K 8/466* (2013.01); *A47K 7/03* (2013.01); *A61K 8/02* (2013.01); *A61K 8/42* (2013.01); *A61K 8/463* (2013.01); *A61K 8/602* (2013.01); *A61K 8/731* (2013.01); *A61Q 19/10* (2013.01); *C11D 3/48* (2013.01); *A61K 2800/28* (2013.01); *A61K 2800/524* (2013.01); *A61K 2800/87* (2013.01); *A61Q 5/02* (2013.01)

(58) Field of Classification Search
None
See application file for complete search history.

(56) References Cited

U.S. PATENT DOCUMENTS 2,438,091 A 3/1948 Lynch
2,528,378 A 10/1950 Mannheimer
(Continued)

FOREIGN PATENT DOCUMENTS

AU 2009100380 A4 6/2009
CN 1046273 10/1990
(Continued)

OTHER PUBLICATIONS

PCT International Search Report and Written Opinion for PCT/US2012/032054 dated Jul. 4, 2012.
(Continued)

*Primary Examiner* — Necholus Ogden, Jr.

(57) ABSTRACT

Multi-use personal care compositions and articles can include a surfactant, a water insoluble hygroscopic fine, fiber, or filament, and a preservative, where such compositions and articles can show an improved preservative property versus unpreserved compositions.

13 Claims, 10 Drawing Sheets

Related U.S. Application Data on Jun. 27, 2013, provisional application No. 61/840,157, filed on Jun. 27, 2013, provisional application No. 61/918,739, filed on Dec. 20, 2013, provisional application No. 61/840,120, filed on Jun. 27, 2013, provisional application No. 61/886,508, filed on Oct. 3, 2013.

(51) Int. Cl.

| | | |
|---|---|---|
| A61Q 19/10 | (2006.01) | |
| A61K 8/42 | (2006.01) | |
| C11D 3/48 | (2006.01) | |
| A61K 8/02 | (2006.01) | |
| A61K 8/60 | (2006.01) | |
| A61K 8/73 | (2006.01) | |
| A61Q 5/02 | (2006.01) | |

(56) References Cited

U.S. PATENT DOCUMENTS

| | | |
|---|---|---|
| 2,658,072 A | 11/1953 | Kosmin |
| 3,689,437 A | 9/1972 | McLaughlin |
| 3,949,137 A | 4/1976 | Akrongold |
| 4,181,632 A | 1/1980 | Schebece |
| 4,190,550 A | 2/1980 | Campbell |
| 4,207,198 A | 6/1980 | Kenkare |
| 4,328,131 A | 5/1982 | Carson, Jr. et al. |
| 4,335,025 A | 6/1982 | Barker et al. |
| 4,367,999 A | 1/1983 | Benuzzi |
| 4,510,641 A | 4/1985 | Morris |
| 4,515,703 A | 5/1985 | Haq |
| 4,554,097 A | 11/1985 | Schebece et al. |
| 4,603,069 A | 7/1986 | Haq et al. |
| 4,654,158 A | 3/1987 | Shepherd |
| 4,665,580 A | 5/1987 | Morris |
| 4,735,739 A | 4/1988 | Floyd et al. |
| 4,812,253 A | 3/1989 | Small et al. |
| 4,861,508 A | 8/1989 | Wegener et al. |
| 4,935,158 A | 6/1990 | Aszman et al. |
| 4,953,250 A | 9/1990 | Brown |
| 4,987,632 A | 1/1991 | Rowe et al. |
| 5,066,494 A | 11/1991 | Becher |
| 5,108,642 A | 4/1992 | Aszman et al. |
| 5,132,115 A | 7/1992 | Wolter et al. |
| 5,139,705 A | 8/1992 | Wittpenn, Jr. et al. |
| 5,225,097 A | 7/1993 | Kacher et al. |
| 5,227,086 A | 7/1993 | Kacher et al. |
| 5,262,079 A | 11/1993 | Kacher et al. |
| 5,264,144 A | 11/1993 | Moroney et al. |
| 5,264,145 A | 11/1993 | French et al. |
| 5,308,180 A | 5/1994 | Pournoor et al. |
| 5,312,559 A | 5/1994 | Kacher et al. |
| RE34,692 E | 8/1994 | Becher |
| 5,340,492 A | 8/1994 | Kacher et al. |
| 5,387,362 A | 2/1995 | Tollens et al. |
| 5,393,466 A | 2/1995 | Ilardi et al. |
| 5,433,883 A | 7/1995 | Massaro et al. |
| 5,433,894 A | 7/1995 | Massaro et al. |
| 5,482,643 A | 1/1996 | Chambers et al. |
| 5,487,884 A | 1/1996 | Bissett et al. |
| 5,520,840 A | 5/1996 | Massaro et al. |
| 5,523,017 A | 6/1996 | Moran et al. |
| 5,540,854 A | 7/1996 | Fair et al. |
| 5,648,083 A | 7/1997 | Blieszner et al. |
| 5,652,228 A | 7/1997 | Bissett |
| 5,681,852 A | 10/1997 | Bissett |
| 5,683,971 A | 11/1997 | Rose et al. |
| 5,683,973 A | 11/1997 | Post et al. |
| 5,698,475 A | 12/1997 | Vlasblom |
| 5,702,992 A | 12/1997 | Martin et al. |
| 5,703,025 A | 12/1997 | Zyngier et al. |
| 5,704,723 A | 1/1998 | Salisian |
| 5,756,438 A | 5/1998 | Rau et al. |
| 5,786,311 A | 7/1998 | Zyngier et al. |
| 5,824,296 A | 10/1998 | Dubief et al. |
| 5,888,953 A | 3/1999 | Harris et al. |
| 5,916,856 A | 6/1999 | Massaro et al. |
| 5,919,471 A | 7/1999 | Saferstein et al. |
| 5,968,852 A | 10/1999 | Vlasblom |
| 5,972,860 A | 10/1999 | Eshita et al. |
| 5,985,808 A | 11/1999 | He et al. |
| 6,026,534 A | 2/2000 | Gonda et al. |
| 6,028,042 A | 2/2000 | Chambers et al. |
| 6,063,390 A | 5/2000 | Farrell et al. |
| 6,074,997 A | 6/2000 | Rau et al. |
| 6,153,208 A | 11/2000 | McAtee et al. |
| 6,162,457 A | 12/2000 | Martz |
| 6,206,863 B1 | 3/2001 | Skewes et al. |
| 6,210,694 B1 | 4/2001 | Park |
| 6,217,854 B1 | 4/2001 | Farrell et al. |
| 6,245,343 B1 | 6/2001 | Roulier et al. |
| 6,322,801 B1 | 11/2001 | Lorenzi et al. |
| 6,328,811 B1 | 12/2001 | Martin et al. |
| 6,376,046 B1 | 4/2002 | Hoshino et al. |
| 6,391,835 B1 | 5/2002 | Gott et al. |
| 6,395,691 B1 | 5/2002 | Tsaur |
| 6,428,799 B1 | 8/2002 | Cen et al. |
| 6,467,981 B1 | 10/2002 | Gueret |
| 6,491,928 B1 | 12/2002 | Smith, III |
| 6,491,933 B2 * | 12/2002 | Lorenzi et al. ............... 424/401 |
| 6,491,937 B1 | 12/2002 | Slavtcheff et al. |
| 6,547,468 B2 | 4/2003 | Gruenbacher et al. |
| 6,550,092 B1 | 4/2003 | Brown et al. |
| 6,592,880 B1 | 7/2003 | Jager |
| 6,607,738 B2 | 8/2003 | Salmon et al. |
| 6,607,739 B1 | 8/2003 | Wallo |
| 6,638,527 B2 | 10/2003 | Gott et al. |
| 6,638,611 B2 | 10/2003 | Seth |
| 6,645,611 B2 | 11/2003 | Seth |
| 6,677,294 B2 | 1/2004 | Shaw et al. |
| 6,730,317 B2 | 5/2004 | Gueret |
| 6,737,068 B2 | 5/2004 | Durden |
| 6,753,063 B1 | 6/2004 | Pung et al. |
| 6,783,294 B2 | 8/2004 | Duden et al. |
| 6,835,701 B2 | 12/2004 | Seipel et al. |
| 6,867,380 B2 | 3/2005 | Miki et al. |
| 6,878,380 B2 | 4/2005 | Farrell et al. |
| 6,883,353 B2 | 4/2005 | Goldoni et al. |
| 6,902,338 B2 | 6/2005 | Puvvada et al. |
| 6,903,057 B1 | 6/2005 | Tsaur |
| 6,977,238 B1 | 12/2005 | Wetzel et al. |
| 6,992,054 B2 | 1/2006 | Lee et al. |
| 7,033,964 B2 | 4/2006 | Gillette |
| 7,101,612 B2 | 9/2006 | Lang et al. |
| 7,115,535 B1 | 10/2006 | Smith, III et al. |
| 7,115,551 B2 | 10/2006 | Hasenoehrl et al. |
| 7,229,956 B2 | 6/2007 | Bedford et al. |
| 7,276,459 B1 | 10/2007 | Lang et al. |
| 7,288,513 B2 | 10/2007 | Taylor et al. |
| 7,320,953 B2 | 1/2008 | Grissett et al. |
| 7,335,626 B2 | 2/2008 | Keenan et al. |
| 7,345,014 B2 | 3/2008 | Keenan et al. |
| 7,348,299 B2 | 3/2008 | Keenan et al. |
| 7,381,692 B2 | 6/2008 | Grissett et al. |
| 7,381,693 B2 | 6/2008 | Keenan et al. |
| 7,419,321 B2 | 9/2008 | Tereschouk |
| 7,452,547 B2 | 11/2008 | Lambino et al. |
| 7,462,348 B2 | 12/2008 | Gruenbacher et al. |
| 7,514,071 B2 | 4/2009 | Simon et al. |
| 7,581,273 B2 | 9/2009 | Dobrin et al. |
| 7,584,519 B2 | 9/2009 | Ouellette et al. |
| 7,651,290 B2 | 1/2010 | Bauer et al. |
| 7,674,058 B2 | 3/2010 | Berger Sharp et al. |
| 7,846,462 B2 | 12/2010 | Spadini et al. |
| 7,854,947 B2 | 12/2010 | Cao et al. |
| 7,874,756 B2 | 1/2011 | Nuebel et al. |
| 7,910,119 B2 | 3/2011 | Allef et al. |
| 8,147,853 B2 | 4/2012 | Taylor et al. |
| 8,157,464 B2 | 4/2012 | Prax |
| 8,308,388 B2 | 11/2012 | Guay |
| 8,357,383 B2 | 1/2013 | Spadini et al. |
| 8,475,817 B2 | 7/2013 | Hasenoehrl et al. |
| 8,534,947 B2 | 9/2013 | Prax |

(56) References Cited

U.S. PATENT DOCUMENTS

| | | | |
|---|---|---|---|
| 8,628,706 B2* | 1/2014 | Glenn et al. .................. 264/50 |
| 8,969,390 B2 | 3/2015 | Klug et al. |
| 9,314,651 B2 | 4/2016 | Kroepke et al. |
| 9,554,978 B2 | 1/2017 | McConaughy et al. |
| 9,596,849 B2 | 3/2017 | Klug et al. |
| 2001/0003565 A1 | 6/2001 | Mcosker et al. |
| 2001/0018068 A1* | 8/2001 | Lorenzi et al. ............... 424/443 |
| 2001/0028894 A1 | 10/2001 | Gueret |
| 2002/0178507 A1 | 12/2002 | Goldoni et al. |
| 2002/0192268 A1 | 12/2002 | Alwattari et al. |
| 2003/0079323 A1 | 5/2003 | Ngai |
| 2003/0140439 A1 | 7/2003 | Durden et al. |
| 2003/0143263 A1 | 7/2003 | Durden et al. |
| 2003/0165546 A1 | 9/2003 | Resch et al. |
| 2003/0180242 A1 | 9/2003 | Eccard et al. |
| 2003/0194425 A1 | 10/2003 | Simon et al. |
| 2003/0194445 A1 | 10/2003 | Kuhner et al. |
| 2003/0199404 A1* | 10/2003 | Lorenzi et al. ............... 510/119 |
| 2003/0203010 A1 | 10/2003 | Wallo |
| 2003/0207632 A1 | 11/2003 | Brooks |
| 2003/0228352 A1 | 12/2003 | Hasenoehrl et al. |
| 2004/0115249 A1 | 6/2004 | Raczek et al. |
| 2004/0116017 A1 | 6/2004 | Smith, III et al. |
| 2004/0120992 A1 | 6/2004 | Lorenzi et al. |
| 2004/0147189 A1 | 7/2004 | Smith, III et al. |
| 2004/0170670 A1 | 9/2004 | Smith et al. |
| 2004/0175343 A1 | 9/2004 | Osborne et al. |
| 2004/0176002 A1 | 9/2004 | Siegwart |
| 2004/0237234 A1 | 12/2004 | Young et al. |
| 2004/0237235 A1 | 12/2004 | Visioli et al. |
| 2005/0008680 A1 | 1/2005 | Deckner et al. |
| 2005/0008681 A1 | 1/2005 | Deckner et al. |
| 2005/0009431 A1 | 1/2005 | Chamba et al. |
| 2005/0065047 A1* | 3/2005 | Shefer .................. A61K 8/11 510/141 |
| 2005/0148260 A1 | 7/2005 | Kopacz et al. |
| 2005/0169880 A1 | 8/2005 | Glick et al. |
| 2005/0202068 A1 | 9/2005 | Hasenoehrl et al. |
| 2005/0215458 A1 | 9/2005 | Lalum et al. |
| 2005/0276827 A1 | 12/2005 | Macedo et al. |
| 2005/0276828 A1 | 12/2005 | Grissett et al. |
| 2006/0057175 A1 | 3/2006 | Ciccognani et al. |
| 2006/0097170 A1 | 5/2006 | Prinz et al. |
| 2006/0135026 A1 | 6/2006 | Arendt et al. |
| 2006/0141014 A1 | 6/2006 | Eknoian et al. |
| 2006/0246119 A1 | 11/2006 | Eknoian et al. |
| 2006/0246120 A1 | 11/2006 | Kelly et al. |
| 2007/0048359 A1 | 3/2007 | Bolton |
| 2007/0071797 A1 | 3/2007 | Hernandez-Munoa et al. |
| 2007/0099813 A1 | 5/2007 | Luizzi et al. |
| 2007/0130706 A1 | 6/2007 | Buhrow et al. |
| 2007/0130707 A1 | 6/2007 | Cohen et al. |
| 2007/0253991 A1 | 11/2007 | Glick et al. |
| 2007/0283516 A1 | 12/2007 | Rasmussen et al. |
| 2008/0104787 A1 | 5/2008 | Keenan et al. |
| 2008/0116096 A1 | 5/2008 | Johnson et al. |
| 2008/0145388 A1 | 6/2008 | Roreger et al. |
| 2008/0168748 A1 | 7/2008 | McCloskey |
| 2008/0200890 A1 | 8/2008 | Wood et al. |
| 2008/0247806 A1 | 10/2008 | Todd et al. |
| 2008/0299269 A1 | 12/2008 | Mane et al. |
| 2009/0028808 A1 | 1/2009 | Cetti et al. |
| 2009/0035340 A1 | 2/2009 | Landa et al. |
| 2009/0178692 A1 | 7/2009 | Warr et al. |
| 2009/0246376 A1 | 10/2009 | Gunn et al. |
| 2009/0324520 A1 | 12/2009 | Cetti et al. |
| 2010/0056628 A1 | 3/2010 | Stockel et al. |
| 2010/0130988 A1 | 5/2010 | Bolton |
| 2010/0136079 A1 | 6/2010 | Kelly et al. |
| 2010/0189811 A1 | 7/2010 | Baum et al. |
| 2011/0132792 A1 | 6/2011 | Villalobos |
| 2011/0152384 A1 | 6/2011 | Gunn et al. |
| 2011/0278429 A1 | 11/2011 | Jha et al. |
| 2011/0290904 A1 | 12/2011 | Mane et al. |
| 2011/0305778 A1 | 12/2011 | Caggioni et al. |
| 2012/0028869 A1 | 2/2012 | Crawford et al. |
| 2012/0246851 A1 | 10/2012 | Smith, III et al. |
| 2012/0246852 A1 | 10/2012 | Smith, III et al. |
| 2012/0252715 A1 | 10/2012 | McConaughy et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0064899 A1 | 3/2013 | Schmidt et al. |
| 2013/0118518 A1 | 5/2013 | Spadini et al. |
| 2013/0266622 A1 | 10/2013 | Mcconaughy et al. |
| 2015/0000058 A1 | 1/2015 | McConaughy et al. |
| 2015/0005221 A1 | 1/2015 | McConaughy et al. |
| 2015/0005223 A1 | 1/2015 | McConaughy et al. |
| 2016/0324732 A1 | 11/2016 | Smith, III et al. |
| 2017/0079484 A1 | 3/2017 | Smith, III et al. |

FOREIGN PATENT DOCUMENTS

| | | |
|---|---|---|
| CN | 1117835 | 3/1996 |
| CN | 1318622 | 10/2001 |
| CN | 101623246 A | 1/2010 |
| CN | 101966137 A | 2/2011 |
| CN | 102551580 A | 7/2012 |
| CN | 102552060 A | 7/2012 |
| DE | 19744213 | 4/1999 |
| DE | 20017205 | 12/2000 |
| DE | 20304298 | 6/2003 |
| DE | 10301838 | 7/2004 |
| DE | 202004007851 | 8/2004 |
| EP | 0032793 B1 | 3/1984 |
| EP | 0047116 B1 | 7/1985 |
| EP | 0161911 | 11/1985 |
| EP | 0211664 | 2/1987 |
| EP | 0272492 A2 | 6/1988 |
| EP | 0353013 | 1/1990 |
| EP | 387693 | 9/1990 |
| EP | 387694 | 9/1990 |
| EP | 0863201 A2 | 9/1998 |
| EP | 1000605 A2 | 5/2000 |
| EP | 1106165 | 6/2001 |
| EP | 1153554 A1 | 11/2001 |
| EP | 1 393 713 A1 | 3/2004 |
| EP | 1 964 541 A1 | 9/2007 |
| EP | 2105061 | 9/2009 |
| EP | 2 176 067 B1 | 4/2010 |
| FR | 1190521 | 10/1959 |
| FR | 2822045 | 9/2002 |
| FR | 2855741 | 12/2004 |
| GB | 2163947 A | 3/1986 |
| GB | 2222526 A | 3/1990 |
| JP | 61277608 A2 | 12/1986 |
| JP | 02265516 | 10/1990 |
| JP | 08084684 | 4/1996 |
| JP | 09299271 | 11/1997 |
| JP | 10000170 | 1/1998 |
| JP | 10183194 A1 | 7/1998 |
| JP | 2002142857 | 5/2002 |
| JP | 2002275031 | 9/2002 |
| JP | 2002315689 | 10/2002 |
| JP | 2002-325697 A | 11/2002 |
| JP | 2002-326902 A | 11/2002 |
| JP | 2003-40718 A | 2/2003 |
| JP | 2003-155225 A | 5/2003 |
| JP | 2004016560 | 1/2004 |
| JP | 2004236996 | 8/2004 |
| JP | 2006082263 | 3/2006 |
| JP | 2006130194 | 5/2006 |
| JP | 2009292750 | 12/2009 |
| JP | 2010046129 | 3/2010 |
| JP | 2012-214395 A | 11/2012 |
| JP | 2013-10728 A | 1/2013 |
| KR | 20060110590 A | 10/2006 |
| KR | 2011-0007508 A | 1/2011 |
| SE | 8703015 | 2/1989 |
| WO | 95/00116 | 1/1995 |
| WO | 95/11887 | 5/1995 |
| WO | 95/26710 A1 | 10/1995 |
| WO | 96/31187 | 10/1996 |
| WO | 97/04683 | 2/1997 |

(56) References Cited

FOREIGN PATENT DOCUMENTS

| | | |
|---|---|---|
| WO | 98/16108 A1 | 4/1998 |
| WO | 98/27193 A1 | 6/1998 |
| WO | 98/28399 A1 | 7/1998 |
| WO | 98/47372 A1 | 10/1998 |
| WO | 98/47469 A1 | 10/1998 |
| WO | 99/31184 | 6/1999 |
| WO | 99/41068 A1 | 8/1999 |
| WO | 01/00021 A1 | 1/2001 |
| WO | 01/08655 A1 | 2/2001 |
| WO | 01/08658 A1 | 2/2001 |
| WO | 01/72262 A2 | 10/2001 |
| WO | 02/24699 A1 | 3/2002 |
| WO | 02/49604 A1 | 6/2002 |
| WO | 02/067887 A2 | 9/2002 |
| WO | 02/089759 A1 | 11/2002 |
| WO | 03/053397 | 7/2003 |
| WO | 2005/059214 A2 | 6/2005 |
| WO | 2005/107695 A1 | 11/2005 |
| WO | 2006/036976 | 4/2006 |
| WO | 2007/098135 A2 | 8/2007 |
| WO | 20071093830 A1 | 8/2007 |
| WO | 2008/002646 A2 | 1/2008 |
| WO | 2008/007425 A1 | 1/2008 |
| WO | 2008/113973 A1 | 9/2008 |
| WO | 2008/157847 A1 | 12/2008 |
| WO | 2009/070736 A1 | 6/2009 |
| WO | 2009/080306 A1 | 7/2009 |
| WO | 2009/146800 A2 | 12/2009 |
| WO | 2010/022393 A1 | 2/2010 |
| WO | 2010/091415 A1 | 8/2010 |
| WO | 2010/139365 A1 | 12/2010 |
| WO | 2011/022345 A1 | 2/2011 |
| WO | 2011/023573 A1 | 3/2011 |
| WO | 2011/156551 A1 | 12/2011 |
| WO | 2012/080153 A1 | 6/2012 |
| WO | 2012/084649 A1 | 6/2012 |
| WO | 2012/131177 A1 | 10/2012 |

OTHER PUBLICATIONS

PCT International Search Report and Written Opinion for PCT/US2012/032111 dated Dec. 17, 2012.
International Search Report and Written Opinion of PCT/US00/01387 dated Sep. 20, 2000.
International Search Report and Written Opinion of PCT/US2012/050873 dated Dec. 10, 2012.
International Search Report and Written Opinion of PCT/US2012/050874 dated Dec. 12, 2012.
International Search Report and Written Opinion of PCT/US2012/050877 dated Dec. 6, 2012.
International Search Report and Written Opinion PCT/US2014/044216 dated Sep. 17, 2014, 10 pages.
International Search Report and Written Opinion, PCT/US2014/044217 dated Sep. 17, 2014, 11 pages.
Photographs of Johnson's Super Sudzer e-z grip soap purchased from Kroger stores around Aug. 2010 and believed to have been on the market in the US at least a year before the filing date of this application.
Photographs of Jonson's Buddies, easy-grip sudzing bar purchased from Target stores around Aug. 2010 and believed to have been on the market in the US at least a year before the filing date of this application.
U.S. Appl. No. 15/429,225, filed Feb. 10, 2017, Edward Dewey Smith, III et al.
U.S. Appl. No. 15/380,478, filed Dec. 15, 2016, Shawn David McConaughy et al.
U.S. Appl. No. 29/459,273, filed Jun. 27, 2013, Lauren May Althaus et al.
U.S. Appl. No. 29/459,274, filed Jun. 27, 2013 Lauren May Althaus et al.

\* cited by examiner

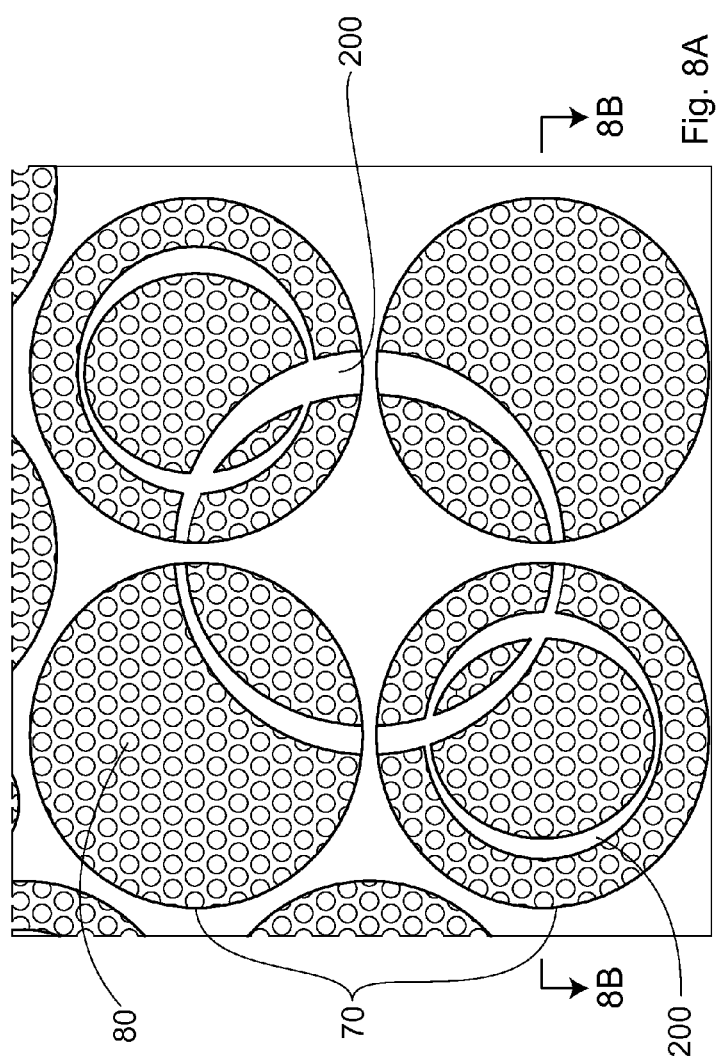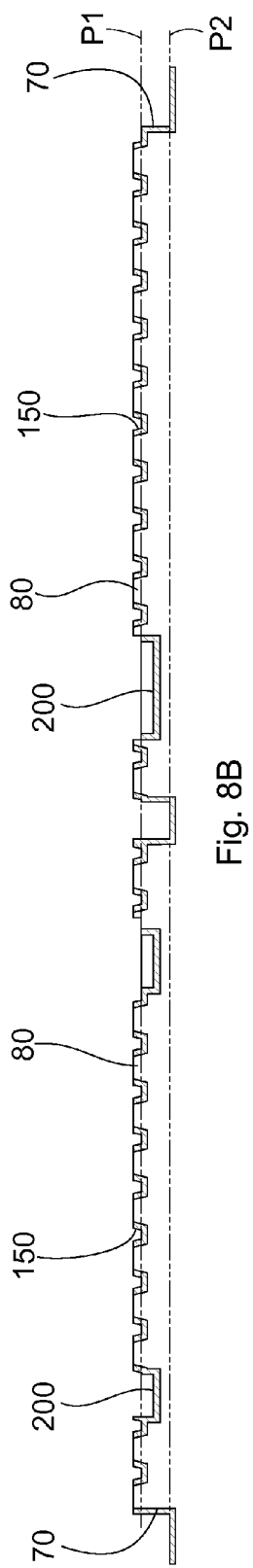
Fig. 8A
Fig. 8B

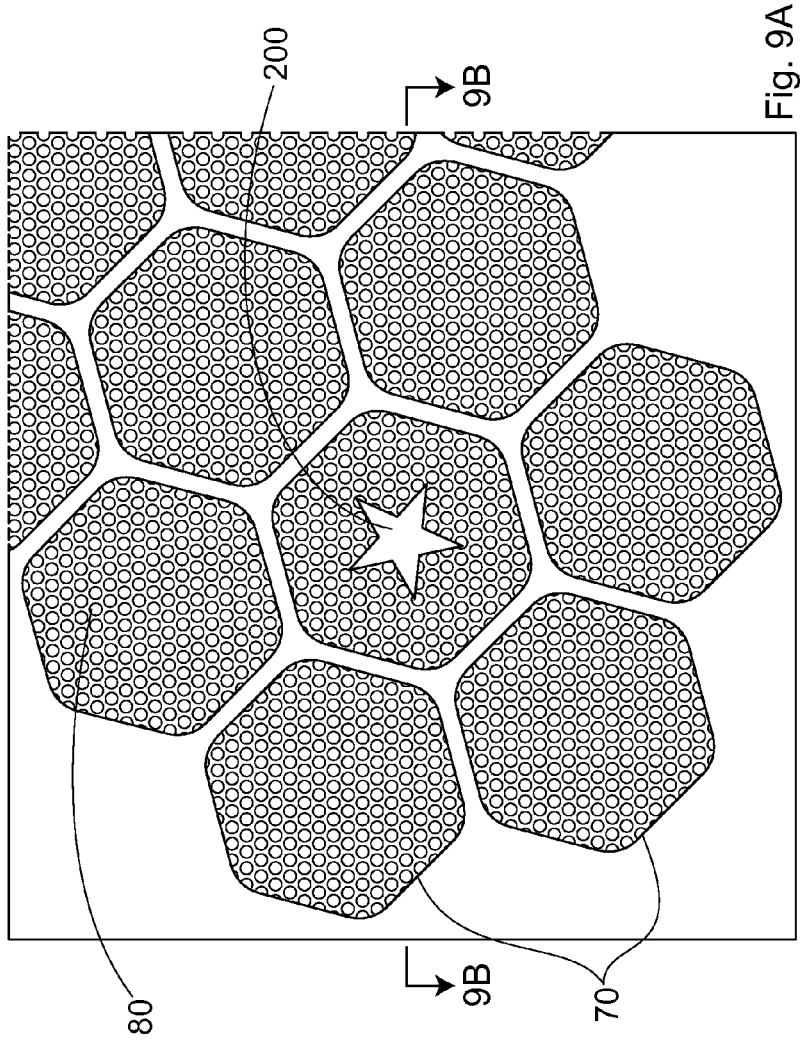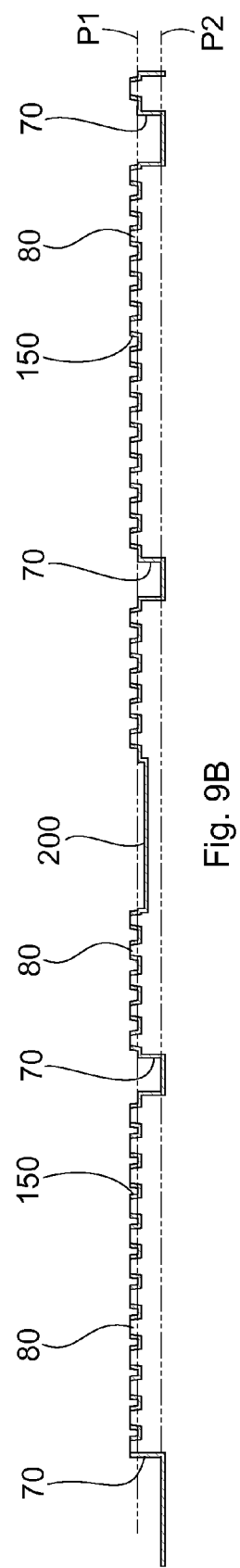

US 9,855,203 B2

PRESERVING PERSONAL CARE COMPOSITIONS

FIELD

This application is directed to personal care compositions, articles, and methods relating thereto.

BACKGROUND

Personal cleansers are a common way to remove dirt and soil from skin and hair. However, the cleansers and the implements often used to apply them can become a source of microbial contamination. As such, a need exists for preserving the cleansers.

SUMMARY

A multi-use personal care composition, comprising: from about 20% to about 80%, by weight of the composition, of a surfactant; from about 3% to about 40%, by weight of the composition, of a water insoluble hygroscopic fiber, fine, or filament; a preservative with a log water solubility of less than 0 to about −5.0, and a solvent; wherein the composition has a compliance value of about 0.01 kg/mm to about 1.5 kg/mm before a simulated use; a water activity of about 0.90 or more after 2 simulated uses; and a consumption rate of 1.0 g/use to about 10 g/use.

A multi-use personal care article, comprising: a composition comprising: a surfactant; from about 3% to about 40%, by weight of the composition, of a water insoluble hygroscopic filament comprising a fiber and a fine; a first preservative with a log water solubility of less than 0 to about −5.0; and a second preservative with a log water solubility of 0 to about 1; and a water penetrable substrate; wherein the composition is at least partially surrounded by the substrate, the composition has a water activity of about 0.90 or more after 2 simulated uses and a consumption rate of 1.0 g/use to about 10.0 g/use; and the article has a compliance value of about 0.03 kg/mm to about 1.5 kg/mm before a simulated use.

A multi-use personal cleansing article, comprising: from about 40% to about 99.6%, by weight of the article, of a soft solid cleansing composition, comprising; from about 20% to about 80%, by weight of the composition, of a surfactant comprising cocoamide monoethanolamine, cocoamidopropyl betaine, decyl glucoside, lauryl glucoside, an alkyl sulfate, an alkyl sulfonate, or a combination thereof; from about 3% to about 40%, by weight of the composition, of a fine, fiber, or filament, comprising cellulose; a solvent; a first preservative comprising an organic acid, citric acid, salicylic acid, sorbic acid, zinc pyrithione, or a combination thereof; and a second preservative comprising methylisothiazolinone, sodium benzoate, or a combination thereof; and a water insoluble substrate at least partially surrounding the composition; wherein the article has a compliance value of about 0.1 kg/mm to about 1.5 kg/mm after two simulated uses and a consumption rate of 1.0 to about 10.0 g/use; and the composition has a water activity of about 0.90 or more after two simulated uses.

BRIEF DESCRIPTION OF THE DRAWINGS

FIG. 8A is a top perspective view of an exemplary substrate;

FIG. 8B is a cross sectional view of the exemplary substrate of FIG. 8A, along line 8B-8B;

FIG. 9A is a top perspective view of another exemplary substrate;

FIG. 9B is a cross sectional view of the exemplary substrate of FIG. 9A, along line 9B-9B;

DETAILED DESCRIPTION OF THE INVENTION

Figure 1:
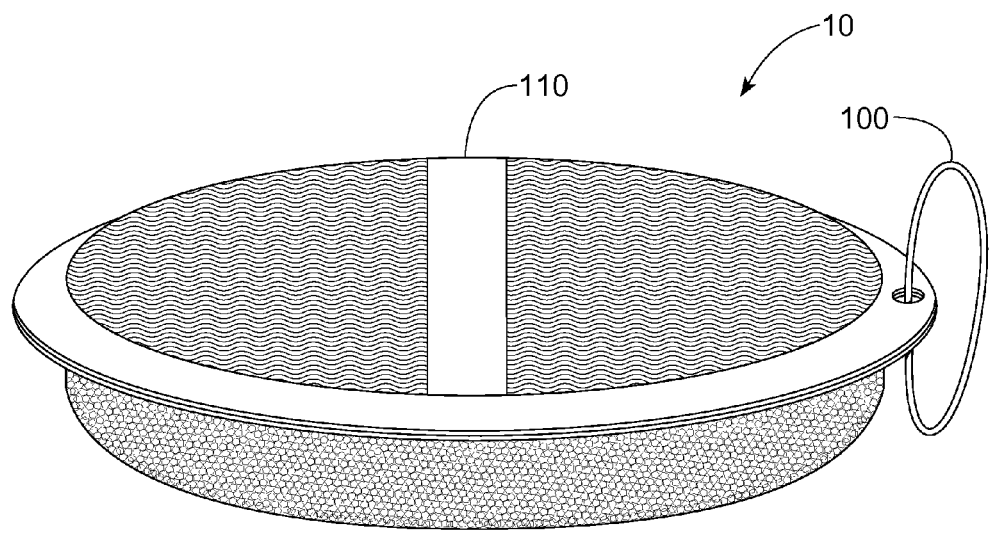
FIG. 1 depicts a perspective view of an example of a personal care article.

This application claims the benefit of U.S. Provisional Application Ser. Nos. 61/840,084; 61/840,157; 61/918,739, 61/840,120, 61/886,502, and 61/886,508, the entirety of which are incorporated by reference herein.

As used herein, the following terms shall have the meaning specified thereafter:

"Cellulose" as used herein refers to cellulose in the form of fines, fibers, and/or filaments; and/or aggregates thereof.

"Compliant" as used herein refers to an article and/or composition with a compliance value of about 1.5 kg/mm or less as measured according to the Compliance Test set out below.

"Fiber" as used herein refers to an elongate particulate having an apparent length exceeding its apparent diameter, i.e. a length to diameter ratio of about 7 or more. Fibers having a non-circular cross-section and/or tubular shape are common; the "diameter" in this case may be considered to be the diameter of a circle having cross-sectional area equal to the cross sectional area of the fiber. "Fiber length", "average fiber length" and "weighted average fiber length", are terms used interchangeably herein all intended to represent the "Length Weighted Average Fiber Length". Fiber length and diameter can be measured in accordance with standard procedures and machinery, like a STFI FiberMaster available from Innventia AB, Sweden. The recommended method for measuring fiber length using this instrument is essentially the same as detailed by the manufacturer of the Fiber Master in its operation manual.

"Filament" as used herein refers to a combination of fibers and fines.

"Fine" as used herein refers to both primary and secondary fines (unless otherwise noted) which are water insoluble materials that pass through a 200 mesh screen under conditions defined in the TAPPI method T-261(80).

"g/use" refers to grams per use, which is the unit used for rate of consumption. The method for measuring and/or calculating the rate of consumption is described herein.

"Granular" refers to a composition comprising discrete particles that are free to move relative to one another and having a bulk density about 20% or more lower than the density of the particles themselves. The particles may have the same composition or may be different.

"Land" area is a generally flattened area existing within a plane and is generally impermeable, existing pores in that area are usually sealed off in the manufacturing process. While the land area is generally flat, there is no requirement that it be perfectly flat and it could itself contain some patterning. Patterning could include, for example, creating roughness in order to reduce the gloss of the substrate.

"Microbial colony forming units" are defined as an aggregate of microbial cells derived from a single progenitor cell.

"Minimum bactericidal concentration" is the lowest concentration of an ingredient required to kill a particular microorganism and is further defined as the minimum concentration needed to cause greater than a 3 log reduction of microbial colony forming units in an inoculated sample.

"Multi-use" refers to a composition or article that is intended for repeated direct contact with a target application surface, for example, skin or hair.

"Natural" as used herein refers to materials that can be derived from plants, animals, or insects, or materials that can be byproducts of plants, animals, or insects; excluding materials produced by bacteria.

"Personal care" refers to a composition or article for topical application to skin and/or hair. Personal care compositions can be rinse-off formulations, in which the composition can be applied topically to the skin and/or hair and then subsequently rinsed within seconds to minutes of application. The composition could also be wiped off using a substrate.

"Pores" are holes in a substrate to allow passage of components such as water or other fluids, air or other gases and vapors, and/or material components such as surfactant or actives which may be dissolved or suspended in fluids.

"Quantitative microbial analysis" as used herein refers to measuring the number of microbial colony forming units by counting or other direct or indirect means such as respiration and can be measured in accordance with the microbial susceptibility test and microbial content test Method below.

"Reusable" refers to an article that can be used for a number of usage events, such as showers and/or baths, wherein the number of usage events can be about 5 or greater, about 7 or greater, about 10 or greater, about 15 or greater, about 20 or greater, about 25 or greater, or about 30 or greater.

"Simulated use" as used herein, refers to a simulated use as described in the Compliance Test below for measuring compliance after a simulated bath/shower, unless otherwise noted.

"Soft solid" as used herein refers to a compositional form which is viscoelastic, like a dough or a paste, and generally remains together as a single piece during use.

"Surface aberration" refers to a raised portion on a surface of a substrate which can be readily apparent to the naked eye and can form a pattern or design on a surface of a substrate. A surface aberration is not a pore or a protuberance.

"Unit cell" is a repeating geometrical pattern which can be measured along with the dimensions of the land and raised areas or structures within it in order to calculate the fractional amounts of land and raised areas for the substrate. A unit cell can be made up of, for example, surface aberrations, land area, and/or features.

"Usage event" refers to one cycle of the Consumption Test described below.

"Water insoluble" when used in relation to fines, fibers, or filaments, refers to those that do not substantially dissolve when placed in water at 42° C. for 15 minutes.

"Water insoluble substrate" refers to a substrate which does not dissolve before at least 10 simulated uses.

"Water penetrable substrate" refers to a substrate which allows water to pass through it into the personal care article and/or to the composition.

Personal care compositions are often used to help cleanse the skin and/or hair. Personal care compositions can come in many forms and can be applied directly to the target surface or onto an implement that is applied to the target surface. For example, bar soap is a common form of personal cleanser and is often applied to a wash cloth prior to application to the target surface. Cleansing compositions are often micro challenged based on the environment in which they are used and/or stored or how they are formulated. Thus, the compositions being used to cleanse a target surface can actually be a source of microbes for the target surface.

The degree and type of micro challenge can be affected by the system in which the composition is used. For example, body wash is considered a closed system as a discrete amount of composition is removed from a container for each use and thus the remainder of the composition is not exposed to the target surface or excess water from the tub or shower. Thus, this type of system is not repeatedly challenged with direct or intended exposure to micro contamination from a target surface.

A second type of system is an open system. In an open system, the composition or implement is exposed directly to a target surface or surfaces in a cleansing area, like shower or bath walls or counters. An example of a composition used in an open system can include a bar soap. In addition, bar soap can be used directly on the skin or hair exposing it to microbes from those surfaces as well.

The cleansing compositions used within a given system can be classified as either high (about 0.90 or more) or low (less than 0.90) water activity. Water activity describes the availability of water within a composition to support various chemical and biological processes requiring water. Water activity can change during use. For example, a composition may have a low water activity prior to exposure to water and a high water activity after exposure to water. As such, water activity of a composition may be measured before use, after 2 uses, after 3 uses, after 4 uses, after 5 uses, or as designated herein. Unless otherwise stated, water activities of a particular composition given herein are before use.

Compositions with high water activity can allow growth of microorganisms. For example, bacteria can grow at a water activity of about 0.90 or above and fungus can grow at a water activity of about 0.70 or above. Below these water activities, microorganisms generally dehydrate and die. Thus, one way to help control microbe contamination is to formulate a low water activity composition. Bar soaps generally have a low water activity. Additionally, bar soaps tend to have a high pH of about 10.0 or more which is also hostile to microorganisms. So, even though bar soap is part of an open system with repeated exposure to microorganisms, bar soap does not require the addition of a preservative to prevent the proliferation of microorganisms and is generally not preserved in addition to its low water activity. However, body wash generally has a high water activity. So, even though body wash is part of a closed system it is usually preserved to prevent the growth of microorganisms in the composition itself.

There is also a need to preserve multi-use compositions that have a high water activity and are part of an open system. This combination presents both of the problems noted above and a new problem, preservative endurance. So, when a high water activity multi-use composition is used, the preservative can leach out of the composition due to, in some instances, solubility of the preservative. This can essentially leave the composition unpreserved and in a high water activity composition an open system leaves the composition very susceptible to microorganism growth.

As can be seen below, an initial investigation reviewed the use of no preservative in high water activity compositions in open systems. In the testing below in Table 1, the article of Comparative Example 1 was put through five simulated uses. Comparative Example 1 was then split into 4 separate pieces and exposed to one of two pools of microbes. The *Pseudomonas* pool represents microbes often experienced in manufacturing environments and aqueous environments, while the enteric pool represents microbes the product may be exposed to upon consumer use. The non-preserved sample of Comparative Example 1 performed poorly in the challenge and thus demonstrated the need for a preservative in high water activity open systems.

| | Microbial Pool and Microbial Count (cfu/g, log 10) | | | | | |
|---|---|---|---|---|---|---|
| | Pseudomonas | | | Enteric | | |
| | Start | Wk 1 | Wk 2 | Start | Wk 1 | Wk 2 |
| Comparative Example 1 | 5.5, 5.5 | 7.5 | 5.1 | 5.7, 5.8 | 7.6 | 6.2 |

Additional studies examining a higher number of simulated uses (15, 25) were conducted. In these studies, the target composition is inoculated with an initial quantity of colony forming units and is then evaluated for a reduction in the number of colony forming units. Two commercial products were included in the study. Comparative Example 2 is a Johnson's@ Buddies® easy grip sudzing bar which is a low water activity composition which is not preserved. Comparative Example 2 maintains its ability to hinder microbial growth as indicated by the log reduction in colony count at the given time points based on the combination of its maintained low water activity and high pH. Comparative Example 3 is a Spongeables™ 20+ Use Male product which has a low water activity prior to the introduction of water, but becomes high water activity after exposure to water. This product is also not preserved. Comparative example 3 exemplifies a system that starts at low water activity and can reduce microbial counts prior to use but is at high water activity after 2 use cycles and fails to maintain its ability to reduce colony counts.

Inventive example 1 (preserved with a combination of ZPT and Na Benzoate) starts as a low water activity composition, its water activity increases to high water activity during the duration of the test. Contrary to Comparative Example 2, the composition functions against both types of microbes up to 15 cycles and against *pseudomonas* out to 25 cycles. Inventive example 2 demonstrates the effectiveness of salicylic acid out to 25 cycles against both bacterial populations. Inventive Example 3 demonstrates the effectiveness of a more water soluble preservative system in a low consumption rate system.

| | Consumption Rate (g/use) | Simulated Use Cycle | Aw | Week 1 log reduction (cfu/g) | | Week 2 log reduction (cfu/g) | |
|---|---|---|---|---|---|---|---|
| | | | | Enterics | Pseudomonas | Enterics | Pseudomonas |
| Inventive Example 1 | 2.4 | 0 | 0.785 | 4.34 | 4.47 | 4.34 | 4.47 |
| | | 15 | 0.927 | 4.34 | 4.47 | 4.34 | 4.47 |
| | | 25 | 0.914 | 0 | 4.47 | 0 | 4.47 |
| Inventive Example 2 | 2.4 | 0 | 0.875 | 4.34 | 4.47 | 4.34 | 4.47 |
| | | 15 | 0.966 | 4.34 | 4.47 | 4.34 | 4.47 |
| | | 25 | 0.919 | 3.53 | 3.84 | 4.34 | 4.47 |
| Inventive Example 3 | 0.85 | 0 | 0.979 | 4.34 | 4.47 | 4.34 | 4.47 |
| | | 15 | 0.975 | 4.34 | 4.47 | 4.34 | 4.47 |
| | | 25 | 0.977 | 2.79 | 4.47 | 4.34 | 4.47 |
| Comparative Example 2 | Not determined | 0 | 0.652 | 4.34 | 4.47 | 4.34 | 4.47 |
| | | 15 | 0.650 | 4.34 | 4.47 | 4.34 | 4.47 |
| Comparative Example 3 | Not determined | 0 | 0.594 | 4.34 | 4.47 | 4.34 | 4.47 |
| | | 15 | 0.997 | 0 | 0 | 0 | 0 |

In addition to the studies above, a control unpreserved article (Comparative Example 4) and two additional articles (Comparative Example 5 and Inventive Example 4) were used at home in the shower for two weeks. The panelists recorded the number of times they used the given article (as shown below). The unpreserved Comparative Example 4 had a high bacteria plate count. Moreover, an exemplary high water activity composition (Comparative Example 5) in an open system preserved with traditional body wash preservatives sodium benzoate and Kathon™ (methylchloroisothiazoline/methylisothiazoline) also showed a high amount of bacteria. When the remainder of Comparative Example 5 was tested after an average of 14 actual uses, no detectable preservative was found in the remaining composition. Without wishing to be bound by theory, the present inventors surprisingly discovered that the combination of the higher log water solubility of the preservatives and the consumption rate of the article into which the composition comprising them was placed, allowed for the preservatives to be depleted from the composition before the end of the use cycle which enabled bacterial growth. Thus, preservation of a multi-use high water activity composition or article in an open system is impacted by both the consumption rate of the composition or article and the log water solubility of the preservative(s). See, for example, Inventive Example 4 with a lower log water solubility preservative (ZPT) and Comparative Example 5 with a higher log water solubility preservative, where Inventive Example 4 had significantly better performance than Comparative Example 5 even though they have similar consumption rates.

|  | Comparative Example 4 | Comparative Example 5 | Inventive Example 4 |
|---|---|---|---|
| Avg. number of uses during study | 9 | 14 | 18.2 |
| Panelist 1a, 1b, 1c | >1 × 10$^4$ cfu/g | 8000 cfu/g | <2000 cfu/g |
| Panelist 2a, 2b, 2c | >1 × 10$^4$ cfu/g | <2000 cfu/g | <2000 cfu/g |
| Panelist 3a, 3b, 3c | >1 × 10$^4$ cfu/g | >1 × 10$^6$ cfu/g | <20 cfu/g |
| Panelist 4a, 4b, 4c | >1 × 10$^4$ cfu/g | >5 × 10$^5$ cfu/g | <10 cfu/g |
| Consumption Rate (g/use) | 4.7 | 4.7 | 4.8 |

Further, with respect to zinc pyrithione, it is traditionally used as an anti-microbial benefit agent, meaning, it is expected to be released from the composition and deposited on the target surface to give a benefit like anti-dandruff or other anti-microbial properties. However, it was surprisingly discovered that zinc pyrithione is maintained within the composition after use at a level which positively impacts bacteria amount resulting in a composition that had much lower bacteria counts at higher usage numbers (ex. Inventive Example 4). Of the three after use ZPT prototypes tested, the ZPT remaining in the composition after 16-26 uses was between 0.18% to 0.40% from a starting percentage of 0.40%.

Without being limited by theory, based on the above learnings, it is believed that for preservation of a high water activity multi-use composition or article two things to consider are the log water solubility of the preservative and the consumption rate of the composition or article. For example, a preservative with a high log water solubility would likely be too quickly used up in a composition or article that had a high consumption rate, but could be perfectly acceptable in a composition or article with a low consumption rate. The log water solubility of a preservative is expressed as the logarithm base 10 of the molar solubility of the preservative where the solubility is in units mol/L at 25° C. and is either calculated from experimentally determined solubility in water at the relevant pH or calculated for the charge neutral molecular species using commercially available Chemsilico software (CS log WSo-3.0). A high log water solubility for a preservative is considered to be 0 or greater while a low log water solubility is considered to be less than 0. So, a high log water solubility preservative can have a log water solubility value of from 0, from about 0.1, from about 0.2, from about 0.3, from about 0.4, to about 0.5, to about 0.6, to about 0.7, to about 0.8, to about 0.9, to about 1.0, or any combination thereof. A low log water solubility preservative can have a log water solubility value from less than 0, from about −0.5, from about −1.0, from about −1.5, from about −2.0, from about −2.5, to about −3.0, to about −3.5, to about −4.0, to about −4.5, to about −5.0, or any combination thereof.

Additionally, a high consumption rate for a composition or article is considered to be 1.5 g/use or greater, while a low consumption rate is considered to be less than 1.5 g/use. Consumption rate can be measured in accordance with the Consumption Test below. A high consumption rate composition or article can have a consumption rate of from 1.5 g/use; from 2.0 g/use, from about 3.0 g/use, from about 4.0 g/use, to about 5.0 g/use, to about 6.0 g/use, to about 7.0 g/use, to about 8.0 g/use, to about 9.0 g/use, to about 10.0 g/use, or any combination thereof. A low consumption rate composition or article can have a consumption rate from about 0.3 g/use, to about 0.5 g/use, to about 0.7 g/use, to about 0.9 g/use, to about 1.1 g/use, to about 1.3 g/use, to less than 1.5 g/use, or any combination thereof.

The amount of preservative can also impact the effectiveness of a preservative or mixture of preservatives in a composition and can also be taken into account. The amount of preservative should not go below the respective minimum bactericidal concentration of the preservative in question for a specific combination of log water solubility and consumption rate.

Personal Care Compositions

Personal care compositions come in many forms. One of the more common forms is bar soap. Bar soap is generally non-compliant and rigid. The rigidity of most bar soaps make them difficult to grip making it more difficult to use during cleansing. Rigid bar soaps also have the disadvantage in that only the small part of the surface which directly contacts the skin can be used for cleansing and this surface area is limited by the bar's non-compliant nature. Conventional rigid bar soap has a compliance value of about 2.5 kg/mm or above.

On the other hand, compliant personal care compositions can bend to some degree to more fully contact the target surface, like the body. This can allow for easier handling of the composition by the consumer and more efficient cleansing. For example, if a compliant personal care composition is originally flat with no curve, when applied to an arm for cleansing there would be some amount of bend to better fit to the arm. Likewise, if the composition's shape has a small amount of a curve, when applied to the arm the composition would bend to some degree to more fully contact the arm. Oppositely, if the original personal care composition is curved such that it would not need to bend to fit to a curved surface like the arm, then it would bend to straighten when applied to a less curved surface like an abdomen.

A challenge when trying to formulate compliant personal care compositions is first formulating for the right amount of compliance. The compositions need to be able to be manipulated by the user with an acceptable amount of effort. This acceptable level of compliance was found to be from about 0.01 kg/mm to about 1.5 kg/mm Additional examples of suitable compliance values include from about 0.03 kg/mm to about 1.0 kg/mm; about 0.05 kg/mm to about 0.75 mm/kg; about 0.10 kg/mm to about 0.6 kg/mm; about 0.05 kg/mm to about 0.5 kg/mm; or about 0.10 kg/mm to about 0.30 kg/mm.

Another challenge when formulating compliant compositions is the ability to maintain an acceptable compliance through the life of the composition. As some reusable compliant personal care compositions/articles experience repeated wetting and then drying processes, the compositions can become hard or rigid, see Comparative Example C1 (below) which has a compliance before a simulated use of 0.52 kg/mm, 30 minutes after one simulated use of 0.32 kg/mm, but at 50.5 hours after the one simulated use the compliance value reaches 1.63 kg/mm Thus, the benefits of a compliant composition can be lost after only a single or a few uses resulting in consumer dissatisfaction. Without being limited by theory, this is believed to at least be caused in part by the loss of moisture from the composition which can cause the composition to crack into domains as it dries. This cracking exposes the interior to even more rapid water loss which only exacerbates the problem over time.

One way of looking at whether a composition or article can likely maintain its compliance through the life of an article is to see whether the composition or article has an acceptable compliance level, as noted above, after repeated simulated uses. For example, the composition or article can have an acceptable compliance, after 10 simulated uses, 12 simulated uses, 15 simulated uses, 20 simulated uses, or 25 simulated uses. In one example, the composition or article can have a compliance value of 0.01 kg/mm to about 1.5 kg/mm after 12 hours of drying after 15 simulated uses.

In addition, another factor to consider when developing an acceptable composition or article is its compliance after a long period of non-use. Some compositions or articles can lose their compliance after long periods with no exposure to water, so it can be helpful to also look at whether a composition or article has an acceptable compliance level when measured 48 hours after the last use.

One solution to these problems has surprisingly been the use of hygroscopic filaments in the composition. Hygroscopic filaments are made of fibers and fines. Without wishing to be limited by theory, it is believed the fibers and fines can work together to form a network. This is believed to be contributed to, in part, by the length and aspect ratio of the fibers. The ability to form a network may be an important feature in order to minimize the common tendency of materials to crack when they lose solvent (water drying). Solvent loss causes dimensional changes with materials due to the loss of solvent volume. The composition tends to therefore shrink, crack, or change its density. Shrinking and cracking are common in coatings when solvent is lost, the result of the internal stress created as the solvent volume is lost. It is more desirable for a composition to shrink (which is a flow, or it acts as a viscous material to relax the stress) instead of crack (which is an elastic behavior, not a flow). Cracking opens up fissures allowing even faster solvent loss throughout the composition. Without wishing to be limited by theory, we believe the filament may not allow cracking to occur due to long range order, i.e., network behavior.

The aspect ratio of a fiber describes the relationship between the length and diameter of the fiber and is calculated by dividing end to end length by diameter. Aspect ratios acceptable for fibers used herein can include those above about 9, above about 9.5, above about 10, above about 100, above about 1000, above about 10,000, to about 100, to about 500, to about 1000, to about 10,0000, to about 100,000, to about 300,000, or any combination thereof.

It is also believed that the hygroscopic water insoluble nature of filaments can further contribute to maintaining compliance upon repeated use. Hygroscopic filaments are water loving or hydrophilic by chemistry so may help to retain water in the composition. Additionally, by being water insoluble, certain filaments can remain in the composition even after exposure to water enabling them to continue contributing the properties of the composition through multiple uses instead of dissolving away. Other filaments may partially or fully dissolve during use enabling them to provide order to the composition and provide soluble components that may help plasticize the composition. It may be beneficial for filaments or portions of the filaments to exit an article during use. For example, filaments may exit the article through pores in the substrate and this may work to enhance scrubbing or to give the appearance the article is being depleted as the composition is used over time.

Another property that can have an impact on granular compositions is the angle of repose. The angle of repose is a measure of the flow ability of the particles in a granular composition and can impact processing of a granular composition. The angle of repose can be, for example, less than about 60° as measured by ASTM D6393.

Personal care compositions can comprise a surfactant; and, a hygroscopic fine, a hygroscopic fiber, or a combination thereof (i.e. a hygroscopic filament). The composition can include, for example, from about 1% to about 99.5%, or from about 10% to about 70%, or from about 20% to about 80%, or from about 20% to about 50%, by weight of the composition, of a surfactant or a mixture of surfactants. A surfactant can be, for example, in the form of a solid powder.

Suitable synthetic surfactants for a personal care composition include, for example, sulfates, sulfonates, alkyl sulfates, linear alkyl sulfates, branched alkyl sulfates, linear alkyl ether sulfates, branched alkyl ether sulfates, linear alkyl sulfonates, branched alkyl sulfonates, linear alkyl ether sulfonates, branched alkyl ether sulfonates, alkyl aromatic sulfates, alkyl aromatic sulfonates, isethionates, cocoamide monoethanolamine, cocoamidopropyl betaine, glucosides, decyl glucoside, lauryl glucoside, or a combination thereof.

Some additional suitable synthetic surfactants include, for example, anionic, nonionic, cationic, zwitterionic, amphoteric surfactants, or combinations thereof. For example, the synthetic surfactant can comprise an anionic surfactant. The anionic surfactant can be branched or linear. Examples of suitable linear anionic surfactants include ammonium lauryl sulfate, ammonium laureth sulfate, sodium lauryl sulfate, sodium laureth sulfate, potassium laureth sulfate, sodium lauryl sarcosinate, sodium lauroyl sarcosinate, sodium lauroyl isethionate, sodium cocoyl isethionate, lauryl sarcosine, cocoyl sarcosine, ammonium cocoyl sulfate, potassium lauryl sulfate, or combinations thereof.

The synthetic surfactant can also comprise sodium laureth (n) sulfate, hereinafter SLEnS, and/or sodium trideceth(n) sulfate, hereinafter STnS, where n defines the average moles of ethoxylation. The n for the SLEnS and/or the STnS can range from about 0 to about 8, from about 1 to about 3, about 2, or about 1. It will be understood that a material such as SLEnS or STnS can comprise a significant amount of molecules having no ethoxylate, 1 mole ethoxylate, 2 mole ethoxylate, 3 mole ethoxylate, and so on in a distribution which can be broad, narrow, or truncated. For example, SLE1S can comprise a significant amount of molecules which have no ethoxylate, 1 mole ethoxylate, 2 mole ethoxylate, 3 mole ethoxylate, and so on in a distribution which can be broad, narrow, or truncated and still comprise SLE1S where an average distribution can be about 1. Similarly, ST2S can comprise a significant amount of molecules which have no ethoxylate, 1 mole ethoxylate, 2 mole ethoxylate, 3 mole ethoxylate, and so on in a distribution which can be broad, narrow, or truncated and still comprise ST2S, where an average distribution can be about 2.

The synthetic surfactant can also comprise one or more branched anionic surfactants and monomethyl branched anionic surfactants such as sodium trideceth sulfate, sodium tridecyl sulfate, sodium C12-13 alkyl sulfate, C12-13 pareth sulfate, sodium C12-13 pareth-n sulfate, or combinations thereof.

As described above, the synthetic surfactant can comprise a nonionic surfactant. Nonionic surfactants for use in the composition can include, for example, those selected from the group consisting of alkyl glucosides, alkyl polyglucosides, polyhydroxy fatty acid amides, alkoxylated fatty acid esters, sucrose esters, amine oxides, or mixtures thereof.

The synthetic surfactant can also comprise a cationic surfactant. Cationic surfactants for use in a composition include, but are not limited to, fatty amines, di-fatty quaternary amines, tri-fatty quaternary amines, imidazolinium quaternary amines, or combinations thereof.

The synthetic surfactant can also comprise an amphoteric surfactant. Suitable amphoteric surfactants can include those that are broadly described as derivatives of aliphatic secondary and tertiary amines, in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition can include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. The surfactant included in the personal care composition can comprise, for example, an amphoteric surfactant that can be selected from the group consisting of sodium lauroamphoacetate, sodium cocoamphoactetate, disodium lauroamphoacetate disodium cocodiamphoacetate, and mixtures thereof.

The synthetic surfactant can also comprise a zwitterionic surfactant. Suitable zwitterionic surfactants can include, for example, those that are broadly described as derivatives of aliphatic quaternary ammonium, phosphonium, and sulfonium compounds, in which the aliphatic radicals can be straight or branched chain, and wherein one aliphatic substituent contains from about 8 to about 18 carbon atoms and one contains an anionic group, e.g., carboxy, sulfonate, sulfate, phosphate, or phosphonate. In one example, the zwitterionic surfactant included in the composition can comprise one or more betaines such as cocoamidopropyl betaine.

The surfactant may also comprise a soap. The composition can include, for example, from about 20% to about 99.5%, from about 20% to about 75%, from about 20% to about 50%, or any combination thereof, by weight of the composition, of a soap.

The soap can include, for example, alkali metal or alkanol ammonium salts of alkane- or alkene monocarboxylic acids. Sodium, magnesium, potassium, calcium, mono-, di- and tri-ethanol ammonium cations, or combinations thereof, can be suitable. In one example, the soap comprises a sodium soap. In another example, the soap comprises a sodium soap and from about 1% to about 25% of at least one of ammonium, potassium, magnesium, and calcium soap. Suitable soaps can also include the well-known alkali metal salts of alkanoic or alkenoic acids having from about 12 to 22 carbon atoms, from about 12 to about 18 carbon atoms; or alkali metal carboxylates of alkyl or alkene hydrocarbons having from about 12 to about 22 carbon atoms.

The composition can also include soaps having a fatty acid distribution of coconut oil that can provide a lower end of a broad molecular weight range or a fatty acid distribution of peanut or rapeseed oil, or their hydrogenated derivatives, which can provide an upper end of the broad molecular weight range.

A soap in the composition can also include, for example, a fatty acid distribution of tallow and/or vegetable oil. The tallow can include fatty acid mixtures that typically have an approximate carbon chain length distribution of 2.5% C14, 29% C16, 23% C18, 2% palmitoleic, 41.5% oleic, and 3% linoleic. The tallow can also include other mixtures with similar distribution, such as the fatty acids derived from various animal tallows and/or lard. According to one example, the tallow can also be hardened (i.e., hydrogenated) to convert part or all of the unsaturated fatty acid moieties to saturated fatty acid moieties.

Suitable vegetable oil can be selected, for example, from the group consisting of palm oil, coconut oil, palm kernel oil, palm oil stearine, and hydrogenated rice bran oil, and mixtures thereof. In one example, the vegetable oil is selected from the group consisting of palm oil stearine, palm kernel oil, coconut oil, and combinations thereof. Suitable coconut oil can include a proportion of fatty acids having 12 carbon atoms or more of about 85%. Such a proportion can be greater when mixtures of coconut oil and fats such as tallow, palm oil, or non-tropical nut oils or fats are used where the principle chain lengths can be C16 and higher. According to one example, the soap included in the composition can be a sodium soap having a mixture of about 67-68% tallow, about 16-17 coconut oil, and about 2% glycerin, and about 14% water.

Soap is often made by a classic kettle boiling process or modern continuous soap manufacturing processes wherein natural fats and oils such as tallow or coconut oil or their equivalents can be saponified with an alkali metal hydroxide using procedures well known to those skilled in the art. Alternatively, the soaps can be made by neutralizing fatty acids such as lauric (C12), myristic (C14), palmitic (C16), or stearic (C18) acids with an alkali metal hydroxide or carbonate.

The personal care composition also comprises a hygroscopic fine, hygroscopic fiber, or a hygroscopic filament. The composition can contain from about 3% to about 40%, by weight of the composition, of the fine, fiber, or filament. Additional acceptable levels can include from about 5% to about 35%, from about 10% to about 30%, or from about 15% to about 25%, by weight of the composition. A filament comprises fibers and fines. A filament can comprise from about 1% to about 95%, by weight of the filament, of fines, and from about 99% to about 5%, by weight of the filament, of fibers; or from about 20% to about 90%, by weight of the filament, of fines, and from about 80% to about 10%, by weight of the filament, of fibers; or from about 50% to about 70%, by weight of the filament, of fines, and from about 50% to about 30%, by weight of the filament, of fibers. A filament may comprise a single type of fiber or multiple types of fibers. A filament may likewise comprise a single type of fine or multiple types of fines.

A fine, fiber, or filament may be, for example, natural, like from a plant or animal, modified natural, or a combination thereof. Examples of animal fines, fibers, or filaments may include wool, silk, and mixtures thereof. Plant fines, fibers, or filaments may, for example, be derived from a plant like wood, bark, oat, corn, cotton, cotton linters, flax, sisal, abaca, hemp, hesperaloe, jute, bamboo, bagasse, kudzu, corn, sorghum, gourd, agave, loofah, or mixtures thereof. One further example of a plant fine, fiber, or filament is a cellulose fine, fiber, or filament. Another exemplary fine, fiber, or filament comprises a regenerated cellulose, like rayon.

Wood pulp fines, fibers, or filaments may include, for example, hardwood pulp or softwood pulp. Non-limiting examples of hardwood pulp filaments include filaments derived from a fiber source selected from the group consisting of: Acacia, Eucalyptus, Maple, Oak, Aspen, Birch, Cottonwood, Alder, Ash, Cherry, Elm, Hickory, Poplar, Gum, Walnut, Locust, Sycamore, Beech, Catalpa, Sassafras, Gmelina, Albizia, Anthocephalus, and Magnolia. Non-limiting examples of softwood filaments include filaments derived from a fiber source selected from the group consisting of: Pine, Spruce, Fir, Tamarack, Hemlock, Cypress, and Cedar.

A fine, fiber, or filament may also be synthetic. Some examples of suitable synthetic hygroscopic fibers, fines, or filaments include nylon, polyester, polyvinyl alcohol, starch, starch derivatives, pectin, chitin, chitosan, cellulose derivatives such as methylcellulose, hydroxypropylcellulose, alkoxy celluloses, or a combination thereof.

The fibers will have a length and diameter. The fibers may have a length weighted average of about 6 cm or less, about 5 cm or less, about 2 cm or less, about 1 cm or less, about 8 mm or less, about 6 mm or less, about 4 mm or less, about 3 mm or less, about 2 mm or less, or about 1 mm or less. The fibers may have an average diameter of about 15 µm, about 20 µm, to about 35 µm, to about 40 µm, or any combination thereof. Fiber length can be used to help determine whether a particular fiber will require more energy to be mixed into a composition. For example, fiber lengths of greater than 1.0 mm were found to require more energy than desired to mix into a composition. Thus, fiber length values of less than 1.0 mm can be used where lower levels of energy are desired to incorporate the fiber into a composition.

The fibers may also have a kink angle. Fiber "kink" is a measurement of an abrupt change in the curvature of a fiber and is defined by the modified Kibblewhite's Kink Index. The angle of this abrupt change is defined as the "kink angle". Kink angle will affect the volume one fiber can occupy, essentially a fiber with a higher kink angle will occupy greater volume filling space more efficiently, this will affect the level of fiber needed to meet the desired compliance value. Exemplary fibers for use herein can have a kink angle or about 35 to about 65, about 40 to about 60, about 45 to about 55, or any combination thereof.

Another property of fibers is the shape factor. The shape factor describes the ratio of the fiber end to end distance as projected in space and the fiber length as measured along the fiber. For instance, a straight fiber will have a high shape factor, since the end to end distance approaches the value of the length along the fiber, while a curly fiber will have a low shape factor. Exemplary fibers for use herein can have a shape factor of about 70 to about 95.

One more property of a fiber is the curl value. The curl value describes the degree of non-straightness of a fiber. The STFI FiberMaster uses the following equation to calculate curl values: Curl value=$[(100/\text{Shape Factor})-1]*100$. Exemplary fibers for use herein can have a curl value of about 10 to about 25.

Fines have a greater surface area and are able to retain more solvent than higher aspect ratio fibers. Thus, fines can be used to help tune the composition or article to the desired compliance value. Fines can also be useful in formulating a composition that will be used up over time. Fines that are smaller than the opening in a substrate can be separated from the composition during use and exit the article through the substrate openings allowing the composition to become smaller during use and helping to signal the end of the life of the composition or article.

Fines may include both primary and secondary fines. Primary fines are naturally produced by the plant or animal source. Secondary fines are derived from fibers, meaning they start as fibers and then are processed into smaller pieces. Secondary fines may be derived, for example, from a natural fiber, like a plant fiber or animal fiber, a modified natural fiber, or a combination thereof. The fiber sources listed above are suitable for their primary fines or for their fibers to be converted into secondary fines and used herein. For example, a fine may comprise cellulose.

Some exemplary cellulose filaments and some of their properties and the properties of the included fibers are below:

| Water insoluble, natural filament | Fiber Length (mm) | Fiber Width (um) | Fiber Shape Factor | Fiber Curl Value | Fiber Kink Angle (deg) | Fiber Kink/mm | Fiber Aspect ratio | Britt Jar Fines (%) |
|---|---|---|---|---|---|---|---|---|
| Example HG1 | 2.776 | 33.5 | 84.5 | 18.3 | 55.79 | 0.29 | 82.9 | <3 |
| Example HG2 | 1.224 | 21.8 | 87.7 | 14.0 | 50.66 | 0.51 | 56.1 | ~20 |
| Example HG3 | 0.760 | 33.1 | 89.7 | 11.5 | 48.73 | 0.48 | 23.0 | 26.2 |
| Example HG4 | 0.403 | 28.4 | 84.7 | 18.1 | 54.56 | 0.95 | 14.2 | 54.3 |
| Example HG5 | 0.350 | 24.9 | 81.6 | 22.5 | 51.75 | 1.03 | 14.1 | 72.3 |
| Example HG6 | 0.287 | 29.5 | 80.5 | 24.2 | 49.59 | 1.23 | 9.7 | 88.6 |

The analysis indicates that for a fixed wt % of filament in the composition (20% for these examples), filament characteristics like % fines, aspect ratio, length, kink/mm, shape factor, and curl value can be used to modify the compliance of an article. Thus, the selection of filament properties can be used to enable a broader range of surfactant systems and concentrations to maintain desired compliant properties. For instance, surfactants with a higher crystallinity have a tendency to have a more rigid structure when in a dried composition. This tendency, however, can combated by selecting a filament with properties that tend to help lower compliance of a composition. These properties are shown in a regression model in FIGS. 10-15.

So, as shown in the regression models, selection of a filament with any of the following properties: lower aspect ratio, shorter length, higher fines %, greater number of kinks/mm, greater shape factor, and/or greater curl value, has a tendency to give a lower compliance composition. Thus, a more crystalline surfactant system could be paired with a filament having one or a combination of those properties in order to balance the more rigid nature of the surfactant system and arrive at an acceptable compliance after drying. Conversely, a less crystalline surfactant system could be paired with filaments having any of the following: higher aspect ratio, longer length, lower fines %, lower number of kinks/mm, lower shape factor, and/or lower curl value, to balance the more fluid nature of this type of surfactant system to arrive at an acceptable compliance after drying.

Certain advantages and disadvantages are present with filament property selection. For example, the use of a filament with shorter fibers and a high fines content enables facile mixing with the surfactant system, however a higher wt % of such filaments may be needed to achieve a desired compliance. Conversely, filaments comprised of longer fibers and a lower wt % of fines can achieve desired compliance values at lower wt % in the composition. However, filaments with longer fibers and lower fines % are more difficult to process and require more energy to mix with surfactant systems. Thus, these properties can also be considered when formulating a personal care composition.

The composition also comprises a preservative. A preservative may be present in an amount of 0.0001% to about 2.0%, by weight of the composition. The preservative may have a low log water solubility of less than 0 or a high log water solubility of 0 or greater. A preservative may have a low log water solubility of less than 0 to about −5.0. A preservative may have a high log water solubility of 0 to about 1.0. Additionally, combinations of high and low log water solubility preservatives may be used.

Some suitable examples of low log water solubility preservatives include metal pyrithiones, organic acids (including but not limited to: undecylenic acid, salicylic acid, dehyroacetic acid, sorbic acid), glycols (including but not limited to: caprylyl glycol, decline glycol), parabens, methylchloroisothiazolinone, benzyl alcohol, ethylenediaminetetraacetic acid, and combinations thereof. Examples of commercially available low log water solubility preservative systems are provided under the tradenames Geogard 111A™, Geoagard221A™, Mikrokill COS™, Mikrokill ECT™, and Glycacil™. Suitable examples of high log water solubility preservatives can include sodium benzoate, methylisothiazolinone, DMDM hydantoin, and combinations thereof. Preservatives are generally present in the composition at about 0.0001% to 2.0%, by weight of the composition. Additionally, the preservatives may be present at levels of about 0.0001%, about 0.001%, about 0.01%, to about 0.50%, to about 1.0%, to about 2.0%, by weight of the composition, or any combination thereof.

Some exemplary preservatives and their log solubility are listed below.

| CAS number | Chemical Name | Log (water Solubility in mol/L) |
| --- | --- | --- |
| 13463-41-7 | Zinc Pyrithione | −4.60 |
| 112-38-9 | Undecylenic Acid | −3.15 |
| 1117-86-8 | caprylyl glycol | −3.08 |
| 94-13-3 | propyl paraben | −2.92 |
| 90-43-7 | Orthophenyl phenol | −2.63 |
| 3380-34-5 | Triclosan | −2.46 |
| 94-26-8 | butyl paraben | −2.43 |
| 120-47-8 | ethyl paraben | −1.91 |
| 1119-86-4 | decylene glycol | −1.90 |
| 22199-08-2 | Silver sulfadiazine | −1.66 |
| 99-76-3 | methyl paraben | −1.43 |
| 69-72-7 | Salicylic acid | −1.41 |
| 60-00-4 | Ethylenediaminetetraacetic acid | −1.40 |
| 520-45-6 | dehydroacetic acid | −1.35 |
| 7761-88-8 | Silver Nitrate | −1.12 |
| 60-12-8 | phenethyl alcohol | −0.83 |
| 26172-55-4 | Methylchloroisothiazolinone | −0.77 |
| 122-99-6 | Phenoxyethanol | −0.64 |
| 100-51-6 | benzyl Alcohol | −0.47 |
| 110-44-1 | sorbic acid | −0.33 |
| 6440-58-0 | DMDM hydantoin | 0.21 |
| 2682-20-4 | Methylisothiazolinone | 0.27 |
| 532-32-1 | Sodium Benzoate | 0.64 |

In order to help with maintaining preservation of the product throughout its life cycle, it can be helpful for at least a portion of the preservative to be maintained in the product after use. For example, about 25% or more of a preservative, by weight of the preservative, can remain in a composition after 15 simulated uses, or even 25 simulated uses. The remaining preservative may be the low log solubility preservative, the high log water solubility preservative, or the combination thereof.

The composition may also comprise a solvent. Solvents for use herein can include, for example, water, glycerin, dipropylene glycol, soybean oil, sucrose polyesters, or combinations thereof. Solvent can be present, for example, in an amount of about 5% to about 50%, about 10% to about 45%, about 15% to about 40%, about 20% to about 35%, or any combination thereof, by weight of the composition.

The composition disclosed herein can also include one or more additional ingredients such as polymers, gums, pluronics, inorganic salts such as zinc carbonate, antimicrobial agents such as zinc pyrithione, actives, brighteners, silica, moisturizers or benefit agents, and emulsifiers.

The composition will also have a consumption rate as measured by the Consumption Test. The composition may have a high consumption rate or a low consumption rate. A high consumption is from about 1.5 g/use to about 10.0 g/use or more. A high consumption rate composition may also be from about 2.0 to about 8.0 g/use, while a low rate of consumption is less than 1.5 g/use.

The composition, for example, can comprise a preservative with a log water solubility of less than 0 and a have a consumption rate of greater than 1.5 g/use; a preservative with a log water solubility of less than −0.25 and a have a consumption rate of greater than 1.5 g/use; a preservative with a log water solubility of less than −0.5 and a have a consumption rate of greater than 2.0 g/use; a preservative with a log water solubility of less than −1.0 and a have a consumption rate of greater than 2.2 g/use.

Conversely, the composition, for example, can comprise a preservative with a log water solubility of greater than about 0 and have a consumption rate of about less than 1.5 g/use; a preservative with a log water solubility of greater than about 0.20 and have a consumption rate of about less than 1.5 g/use.

Personal Care Articles

The above described personal care compositions may also be part of a personal care article. A personal care article comprises a substrate and a personal care composition. A personal care article may contain from about 40% to about 99.6%, by weight of the article, of a personal care composition. Additional acceptable ranges of composition include from about 50% to about 99% or from about 75% to about 98%, by weight of the article. A substrate may at least partially surround a composition or it may surround a composition. The personal care article may also comprise multiple substrates. A substrate may be adjacent to a composition, another substrate, or a combination thereof. A personal care article may comprise a contact substrate, non-contact substrate, or combinations thereof. Contact substrates are those on the exterior of the article likely to make direct contact with the target surface, while non-contact substrates are those not likely to make contact with the target surface. A personal care article may be used, for example, on skin, hair, or both. A personal care article may also be used, for example, for cleansing of the skin, cleansing of the hair, shave preparation, post shave treatment, or a combination thereof. A personal care article may be a personal cleansing article. A personal care article may also be reusable.

Adding a substrate to a personal care composition can present its own challenges. A substrate can change the amount of water available to the composition at the outset which can impact lather, rate of consumption, and surfactant release. A substrate can also change the dynamics with the composition during use. For example, the substrate can retain water in close proximity to the composition. It can also impact the composition after use by, for example, limiting the exposure of the composition to the air to inhibit drying after use. All of these factors can be considered when creating a personal care article and the properties of the composition and the article are balanced so that the article has the desired characteristics. This is especially true where the composition and/or article are to be compliant throughout the lifetime of the article.

A personal care article can be compliant. For example, if the article is a personal care article for cleansing the skin, then the article will bend to some degree to more fully contact a curved body part like the arm. Thus, if the personal care article is originally flat with no curve, when applied to the arm for cleansing there would be some amount of bend to better conform to the arm. Oppositely, if the original article is curved such that it would not need to bend to conform to a curved surface like the arm, then it would bend to straighten when applied to a less curved surface like the abdomen. An article may be fully compliant meaning it is capable of completely conforming to the surface to which it is applied.

Compliance of a personal care article can be measured according to the Compliance Test described in more detail below. A personal care article can comprise a compliance value of about 1.50 kg/mm or less. Additional examples of suitable compliance values include from about 0.01 kg/mm to about 1.5 kg/mm; from about 0.03 kg/mm to about 1.0 kg/mm; about 0.10 kg/mm to about 0.75 mm/kg; about 0.10 kg/mm to about 0.6 kg/mm; about 0.05 kg/mm to about 0.5 kg/mm; or about 0.1 kg/mm to about 0.3 kg/mm.

The article and/or composition can become compliant after exposure to water. Thus, a non-compliant article or composition may, after exposure to a liquid, like water, during use, become compliant. If an article or composition becomes compliant by the end of a second simulated use, then it is considered compliant.

The article will also have a consumption rate as measured by the Consumption Test. The article may have a high consumption rate or a low consumption rate. A high consumption is from 1.5 g/use to about 10.0 g/use or more, while a low rate of consumption is less than 1.5 g/use.

Figure 4:
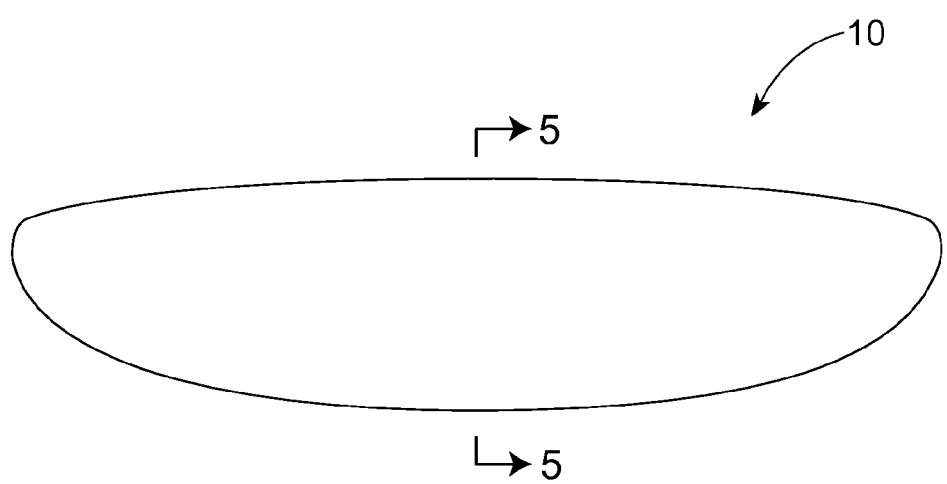
FIG. 4 depicts a side view of a personal care article according to another example.
Figure 5:
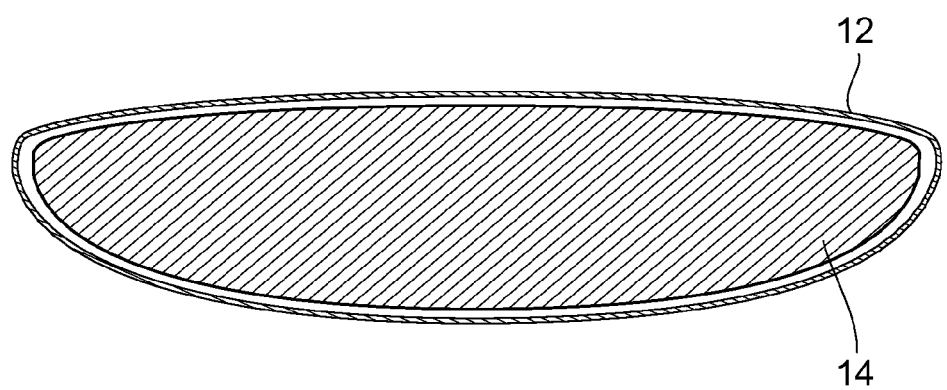
FIG. 5 depicts a cross sectional view of the personal care article of FIG. 4, along line 5-5.

A perspective view of a person care article 10 according to one example is shown in FIG. 1. As shown in FIGS. 4 and 5, a personal care article 10 can comprise a water penetrable first substrate 12 and a personal care composition 14, wherein the water penetrable first substrate 12 is adjacent to the personal care composition 14. The water penetrable first substrate 12 at least partially surrounds the composition 14. In one example, as shown in FIG. 4, a single piece of water penetrable substrate 12 has been wrapped around the personal care composition 14 and sealed (not shown).

Figure 2:
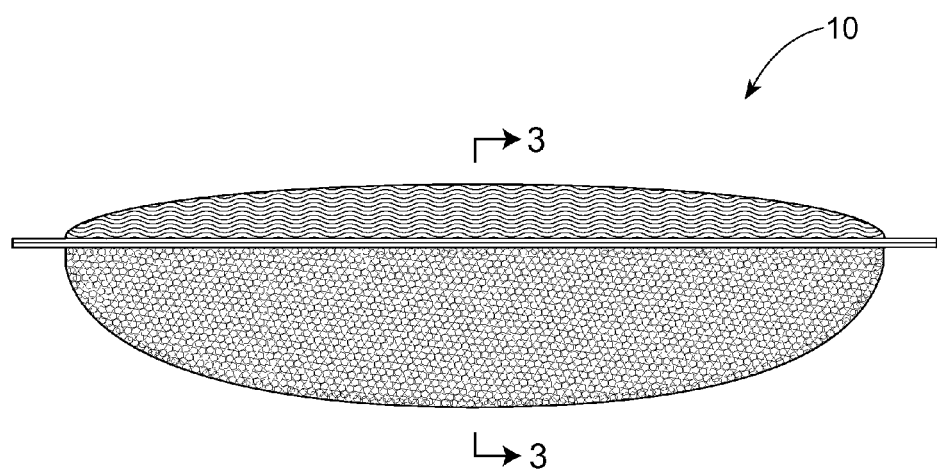
FIG. 2 depicts a side view of a personal care article according to one example.
Figure 3A:
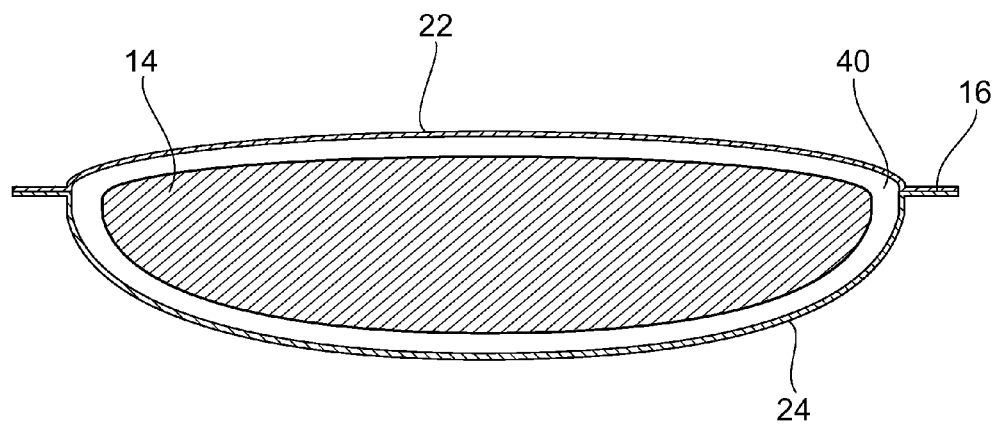
FIG. 3A depicts a cross sectional view of the personal care article of FIG. 2, along line 3-3.

In another example, as illustrated in FIGS. 2 and 3A, a personal care article 10 comprises a personal care composition 14, a first substrate 22 adjacent to the personal care composition 14, and a second substrate 24 adjacent to the personal care composition 14. In one example depicted in FIG. 3A, the seal 16 joining the first and second substrates (22, 24) is only visible on the ends, but actually goes all the way around the personal care composition 14. The first and second substrates (22, 24) may, however, be sealed in other configurations, or, may only be partially sealed so as to form, for example, a pouch. The first and second substrates (22, 24) may be the same or different.

Figure 6:
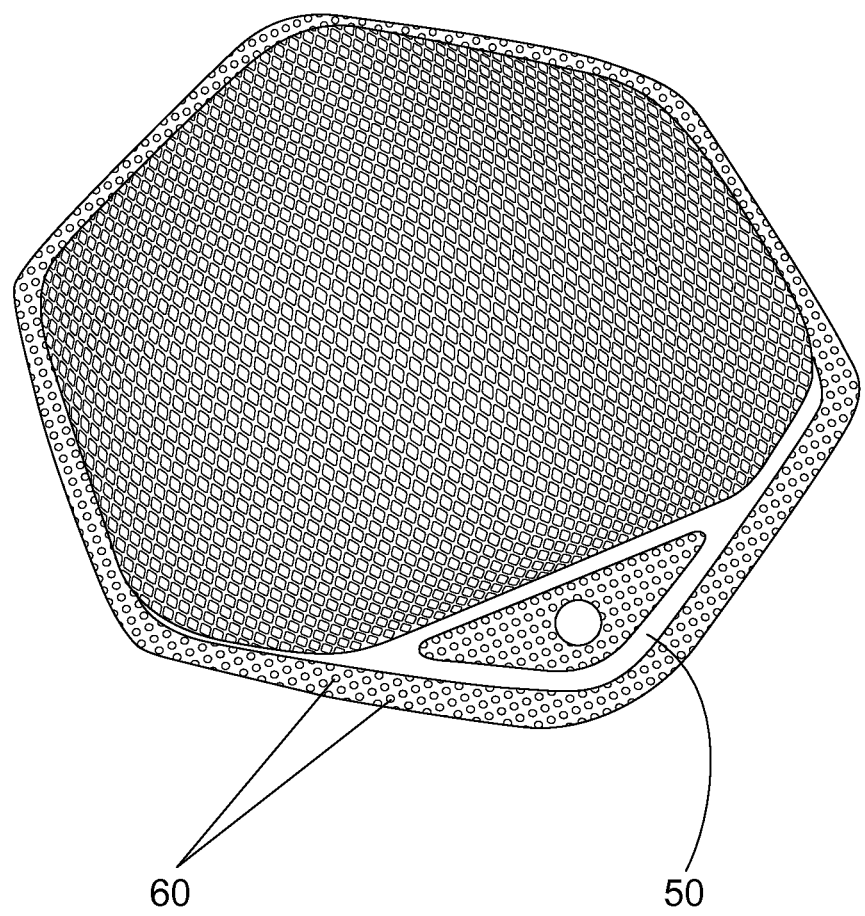
FIG. 6 is a picture of an exemplary personal care article.
Figure 7:
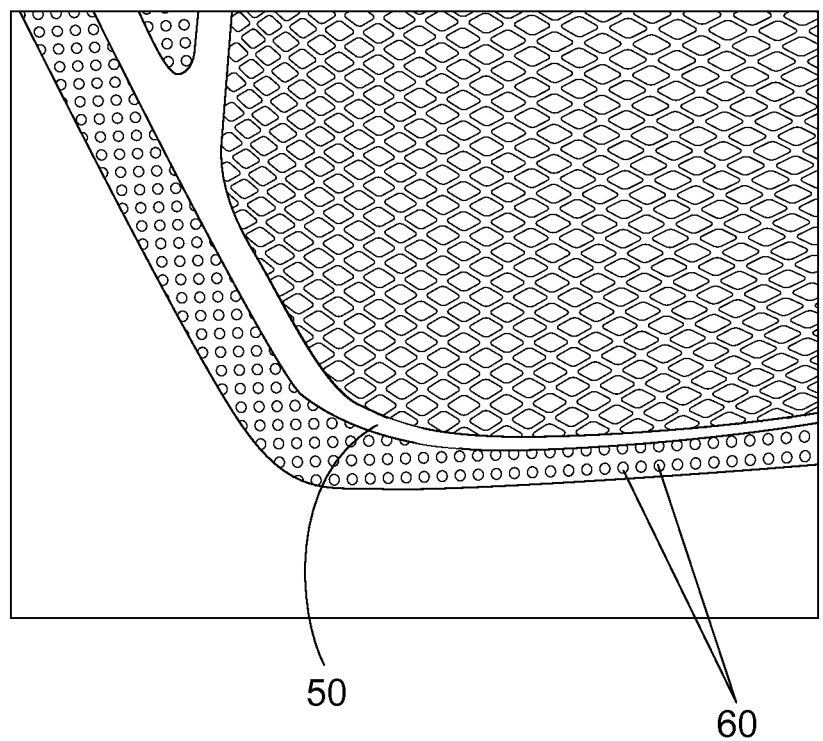
FIG. 7 is a close-up of one corner of the article in FIG. 6.
Figure 10:
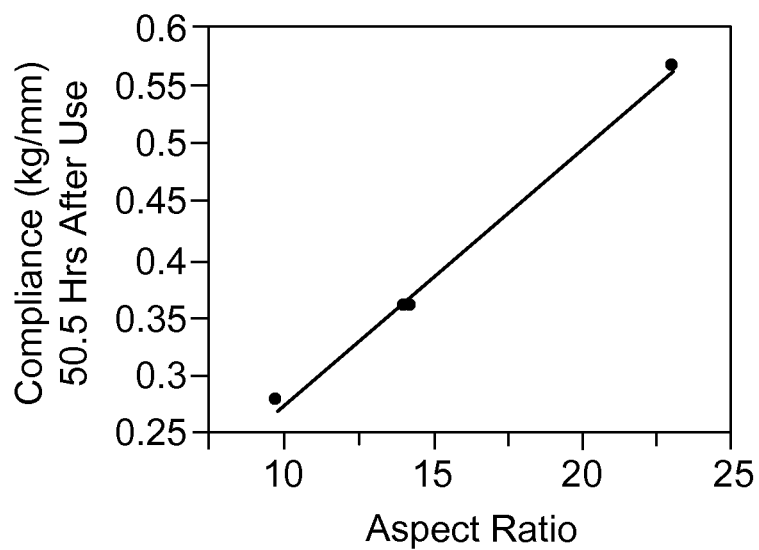
FIG. 10 is a regression of aspect ratio and compliance 50.5 hours after use.
Figure 11:
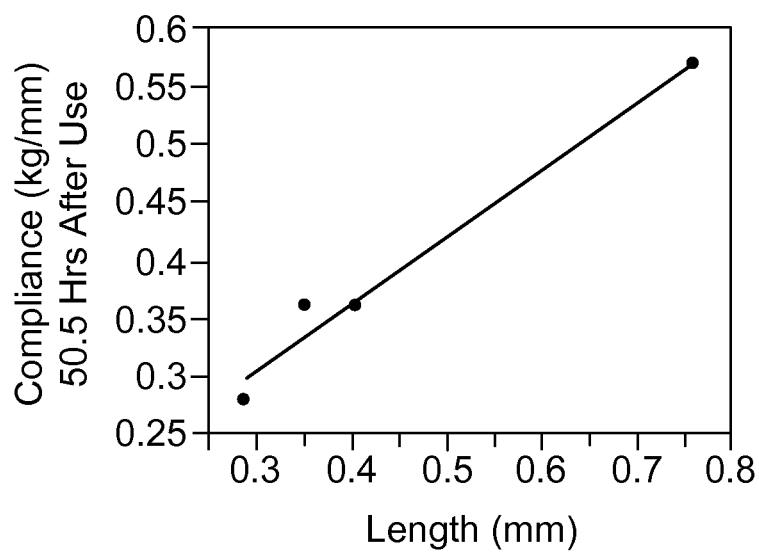
FIG. 11 is a regression of length and compliance 50.5 hours after use.
Figure 12:
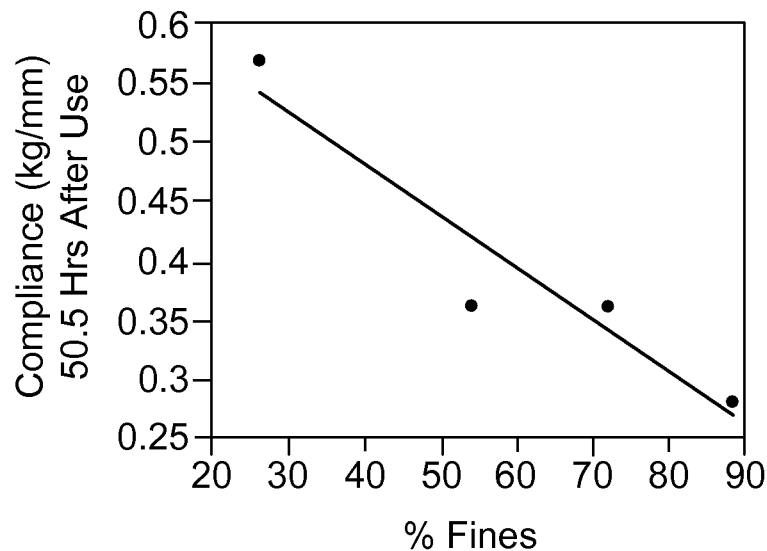
FIG. 12 is a regression of % fines and compliance 50.5 hours after use.
Figure 13:
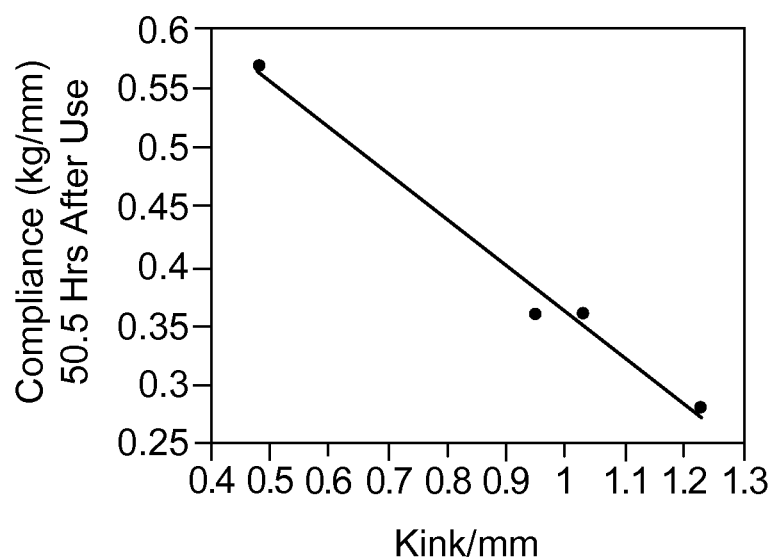
FIG. 13 is a regression of kink and compliance 50.5 hours after use.
Figure 14:
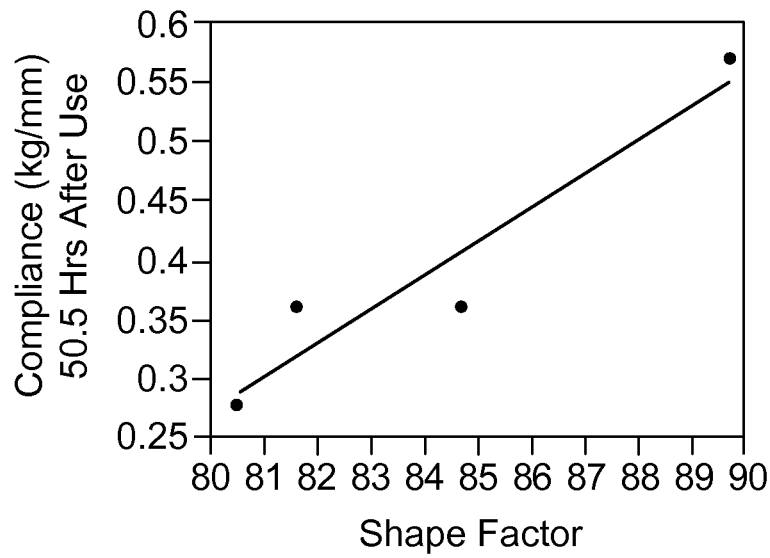
FIG. 14 is a regression of shape factor and compliance 50.5 hours after use.
Figure 15:
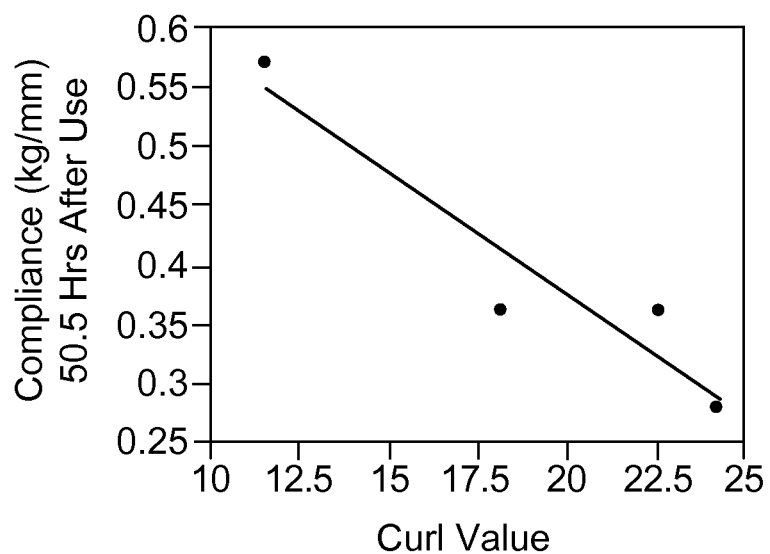
FIG. 15 is a regression of curl value and compliance 50.5 hours after use.

As can be seen in FIGS. 6 and 7, another exemplary form of sealing involves forming a continuous seal 50 internal to the periphery of the article, where the periphery of the article is sealed in a discontinuous manner 60. The continuous seal 50 internal to the periphery of the article prevents bulk loss of composition from the article and provides sufficient seal strength for maintaining the integrity of the article throughout consumer use. Locating the continuous seal 50 internal to the article periphery is advantageous in that a sealed land area creates a thin hard surface, relative to the inherent substrate properties. This thin hard seal surface when located on the article periphery can cause scratching when used by the consumer. The article periphery can also be left unsealed leaving the distinct substrate layers separate, this result in an unfinished appearance which is not consumer preferred. Having a discontinuous seal 60 on the periphery of the article provides a high quality finished appearance that is consumer preferred while eliminating the formation of a thin hard surface on the periphery of the article. For instance, a 4 mm wide discontinuous seal can be created along the periphery of the article, with the discontinuous pattern being 1 mm by 1 mm squares spaced 2 mm apart. In addition, internal to the article periphery, a 1 mm continuous seal can be created. During manufacturing the article can be trimmed within the discontinuous seal creating a finished article with the desired discontinuous seal width while reducing the risk of inadvertently trimming in the continuous seal area and creating an opening for bulk loss of composition from the article.

In another example only a discontinuous seal 60 may be present along the articles periphery. In this example the pattern and width of the seal are designed to restrict bulk loss of composition from the article.

In an additional example, a seal may be continuous, but interrupted (not shown).

Figure 3B:
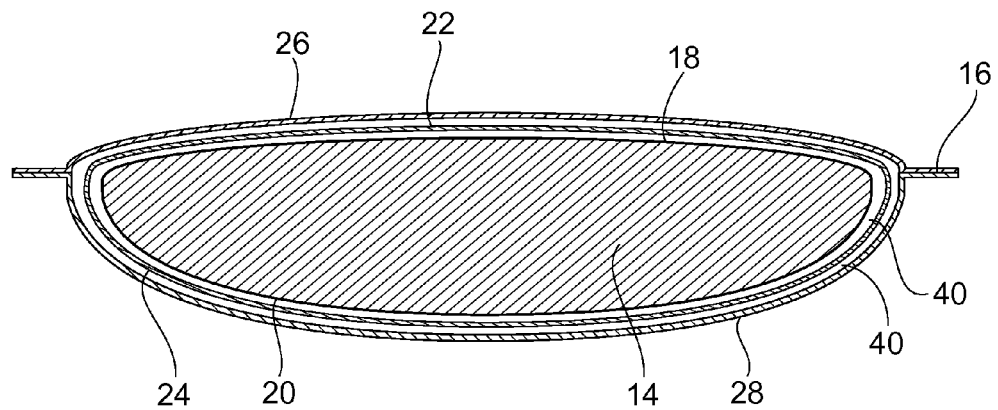
FIG. 3B depicts a cross sectional view of the personal care article of FIG. 2, along line 3-3, where additional substrates have been added.

In another example, as illustrated in FIGS. 2 and 3B, a personal care article 10 comprises a personal care composition 14 having a first side 18 and a second side 20. A first substrate 22 is adjacent to the first side 18, while a second substrate 24 is adjacent to the second side 20. In one example depicted in FIG. 3A, the seal 16 joining the first and second substrates (22, 24) is only visible on the ends, but actually goes all the way around the personal care composition 14. In addition, a first water insoluble substrate 26 is adjacent to the first substrate 22 and a second water insoluble substrate 28 is adjacent to the second substrate 24. The first and second water insoluble substrates (26, 28) may be the same or different. Like the seal of the first and second substrate (22, 24), while only visible on the ends, the seal 16 of the first and second water insoluble substrates (26, 28) goes all the way around the personal care composition 14. The seal 16 of the first and second water insoluble substrate (26, 28) may, however, be sealed in other configurations, or, may only be partially sealed so as to form, for example, a pouch.

The personal care article may also comprise a chamber 40, as seen, for example, in FIGS. 3A and 3B. A chamber is an open area between a substrate and a personal care composition or between a substrate and another substrate, where the substrate is not touching the personal care composition or the other substrate. The substrate(s) may be flexible such that they touch the composition (or another substrate) in some areas and not others. The areas where the substrate is touching or not touching the composition or other substrate may shift as the substrate(s) and composition shift during handling and/or use.

The personal care article can include from about 0.5% to about 25,000%, by weight of total substrate(s), of a personal care composition. In one example, the article comprises greater than 3,500%, by weight of the total substrate(s), of a composition. In other examples, the article comprises greater than 4,000%, by weight of the total substrate(s), of a composition; greater than 4,250%, by weight of the total substrate(s), of a composition; greater than 4,500%, by weight of the total substrate(s), of a composition; greater than 4,750%, by weight of the total substrate(s), of a composition; greater than 5,000%, by weight of the total substrate(s), of a composition; or any combination thereof.

The personal care article may be in any suitable shape, for example, oval, square, rectangular, circular, triangular, hour glass, hexagonal, c-shaped, etc. Furthermore, the article can be sized based upon the desired use and characteristics of the article. An article can range in surface area size, for example, from about a square inch to about hundreds of square inches. An article can also have a surface area of, for example, about 5 $in^2$ to about 200 $in^2$, from about 6 $in^2$ to about 120 $in^2$, or from about 15 $in^2$ to about 100 $in^2$. An article may also have a certain thickness, for example, of from about 0.5 mm to about 50 mm, from about 1 mm to about 25 mm, or preferably from about 2 mm to about 20 mm There may also be multiple compositions within zones in the article. These are described more fully in U.S. Pat. App. Pub. Nos. 2013/0043145, 2013/0043146, and 2013/0043147.

A substrate can also comprise a feature. Substrate features can include, for example, design elements such as shapes and letters. Substrate features may reside, for example, within the land portions, the surface aberrations, or a combination thereof and may be located in plane, above plane, or below plane, or combinations thereof relative to either the land portion or surface aberration. Substrates with features out of plane with both the land and surface aberration portions are considered multiplanar substrates. Examples of features can be seen in FIGS. 8 (the "O"'s) and 9 (the stars).

The article 10 may further comprise a hanger 100, see FIG. 1. A hanger 100 will allow the article 10 to be suspended. Suitable hangers can include chords, hooks, loops, twines, strings, elastic bands, etc. and can comprise synthetic/and or natural materials including fibers, and can be molded such as injection molded. A hanger may be a single piece or multiple pieces fastened together. The multiple pieces could have corresponding male and female elements and the fastening mechanisms could include, for example, snaps, buttons, hook and eye, etc.

The article may also further comprise a use indicator 110, see FIG. 1. A use indicator 110 will help signify to a user when the article 10 has reached or is reaching the end of its useful life. A use indicator can take the form of, for example, a strip which changes color as the article is used. Additional examples of use indicators can include printed inks, dyes, pigments, slot or spray coated polymers containing, for example, inks, dyes or pigments.

A. Substrate

A personal care article can comprise at least one substrate. The substrate can enhance cleansing and therapeutic treatment of a surface such as skin and/or hair. For example, by physically coming into contact with the skin and/or hair, the substrate can aid in the cleansing and removal of dirt, makeup, dead skin, and other debris such that the substrate can act as an efficient lathering and/or exfoliating implement but can also be non-abrasive to the skin. A substrate can be a composite (i.e., there are multiple plies to the substrate which may be of the same or different materials). In one example, the substrate can be water insoluble. In other examples, the substrate can be water penetrable. However, the personal care article can comprise both water penetrable substrates and water insoluble substrates.

Substrates can be arranged in many different configurations on an article. Some examples of these configurations can be found, for example, in U.S. Pat. No. 6,491,928; U.S. Pat. App. Pub. Nos. 2013/0043146; 2012/0246851; 2013/0043145; and 2013/0043147.

A substrate can at least partially surround one or more personal care compositions. In other examples, a substrate can entirely surround one or more personal care compositions. A substrate can be in the form of a pouch, pocket, wrap, or any other suitable configuration. A substrate could also at least partially surround or be adjacent to another substrate, and/or entirely surround another substrate.

The substrate can be, for example, a formed film, like a vacuum formed film. The substrate could be a nonwoven (i.e., a natural or synthetic nonwoven including fibrous and nonfibrous nonwovens), which can typically have land regions (i.e., regions that do not allow water and/or personal care composition to pass through) and openings; a woven; a film (e.g., a formed film); a sponge, which can include a natural and/or synthetic sponge (e.g., polymeric mesh sponge), examples of which can include those described in European Patent Application No. EP 702550A1 published Mar. 27, 1996; a polymeric netted mesh (i.e., a "scrim"), examples of which can include those described in U.S. Pat. No. 4,636,419; a batting; spunbond; spunlace; hydroentangled; carded; needlepunch; or any other suitable material. In certain examples, the substrate can be a composite material that can include, for example, one or more plies of the same or different materials such as nonwovens, wovens, films, sponges, scrims, battings, and the like superimposed physically, joined together continuously (e.g., laminated, etc.) in a discontinuous pattern, or by bonding at the external edges (or periphery) of the substrate and/or at discrete loci. Suitable examples for each type of substrate and other suitable substrate materials are described in U.S. Pat. App. Pub. No. 2012/0246851.

Parameters to consider when selecting substrates (e.g., formed films) can include thickness, pattern, polymer stiffness, and permeability. Additional information on such parameters is also described in U.S. Pat. App. Pub. No. 2012/0246851.

A substrate can include one or more openings such that water, the personal care composition, and/or lather, for example, can pass through the substrate. In one example, where a permeable substrate can be adjacent to the personal care composition, water can pass through the water permeable substrate to interact with the personal care composition. As the personal care composition dissolves, it can then also pass through the substrate to be delivered to a target surface (e.g., skin).

In one example, permeability of openings can be selected based on a dissolution half-life of a personal care composition and a desired reusability of the article. For example, when the dissolution half-life of the personal care composition is high, a higher level of permeability can be selected to counteract the high dissolution half-life and provide a desirable consumption rate for the article. Alternatively, when the dissolution half-life of the personal care composition is low, the permeability of the one or more openings or can be lower and still provide a desirable consumption rate for the article. A substrate can include, for example, a permeability of about 1 opening/$cm^2$ or greater, about 10 openings/$cm^2$ or greater, about 100 openings/$cm^2$ or greater, about 500 openings/$cm^2$ or greater, about 1,000 openings/$cm^2$ or greater, about 1,500 openings/$cm^2$ or greater, or any combination thereof.

The openings can be apertures. For example, the one or more openings can include well-defined apertures such as microapertures or macroapertures, holes, perforations, cavities, raised or depressed fibrous and/or nonfibrous regions, gaps between regions, and the like that can enable, for example, water and/or the personal care composition to pass through the substrate.

A substrate can be a contact substrate, which can be a substrate for contacting a target surface (e.g., skin). A substrate can also be a noncontact substrate. Noncontact substrates, for example, can be used to help give a personal care article a desired consumption rate, softness, lather properties, etc.

A substrate may also comprise a surface aberration 70, as can be seen in FIGS. 8 and 9. A surface aberration can be a raised portion on a surface of a substrate. It can be readily apparent to the naked eye and can form a geometric pattern on a substrate. In one example, the geometric pattern does not require registration on the assembled article.

Surface aberrations can be from about 700 µm to about 7000 µm in height (the z-direction). Surface aberrations can also be macroapertured.

The surface aberrations provide thickness without itself being a single pore, while the conventional portions of the substrate can provide a larger number of pores to promote lather generation. Particularly, multiplanar substrates with a thickness from about 700 µm to about 7000 µm can allow for enough water, surfactant, and air to pass through such that the sufficient lather can be generated.

Surface aberrations can also provide an exfoliation benefit. In order to provide exfoliation with a monoplaner film you need to create pores with a large diameter, in order to achieve a significant z-dimension. This concentrates the applied force over a smaller contact area with the skin, making the substrate feel scratchy. Conversely, multiplanar films contain surface aberrations with larger z-dimensions. These surface aberrations contribute to the exfoliating properties of the film and more directly control the surface area over which the applied force is distributed, reducing the scratchy perception of the substrate. Additionally, by incorporating a minimum number of pores per square inch, about 10 (local), the issue with a scratchy feel related to pore size can also be abated.

Land area of a substrate can impact consumer acceptance of the product. For example, consumers can view films with larger amounts (e.g. about 55% or more) of land area as looking too much like plastic. In order to combat this consumer perception, a substrate may include more surface aberration area (e.g. about 45% or more).

A substrate may include about 45%, about 50%, about 55%, about 60%, about 65%, about 70%, about 75%, to about 50%, about 55%, about 60%, about 65%, about 70%, about 75%, about 80%, about 85%, about 90%, about 95%, about 98%, or any combination thereof, of surface aberration area. The amount of surface aberration area and land area can be determined by measuring the dimensions geometrically in the X-Y (flat planar) direction for the unit cell of the substrates for their planar projection, for example, with a ruler or a caliper. It may be convenient to use a magnifying technique to measure fine dimensions. Surface aberration and land area can be estimated from geometries of processing equipment used to make the structures, which are usually known from design, although these are only estimates since substrates can shrink or stretch during subsequent processing. Thus, land area and surface aberration area are expressed as a percentage of land (or surface aberration) area within a unit cell divided by the total area of the unit cell. Where the pattern on the substrate is irregular such that no unit cell exists, the percentage of land or surface aberration area is expressed as the amount of land (or surface aberration) area of the article surface utilizing the substrate pattern in question divided by the total area of the article surface utilizing the substrate pattern in question. A surface aberration can be part of a unit cell which is generally the smallest repeating unit (other than pores, if applicable). The calculation is determined with the substrate oriented such that the protuberances or pores are in the upward direction, pointing normal to the viewing plane. For instance a circular aberration motif with a diameter of 0.25 mm and a unit cell area of 0.625 mm$^2$ would have a percentage surface area of aberration of approximately 7.85%.

Too much surface aberration area can impact the integrity of a substrate and can, for example, lower the resistance of the substrate to tearing. Thus, the amount of surface aberration area can be balanced among scratchiness, consumer acceptable look, and longevity based on the desired properties of the substrate.

Surface aberrations can be permanent deformations in a substrate, such that after they are formed, no force is required to maintain the raised or depressed state. Surface aberrations can be formed through a process, like, vacuum forming, for example. So, actions like cinching and gathering do not generally form surface aberrations, but puckers in a substrate. These surface aberrations may also contain pores 80. To form a plane, as discussed below, at least some of the surface aberrations will contain at least three protuberances that are not in a row. A surface aberration can have up to about 250,000 protuberances on its surface. A surface aberration can form a pattern or design. For example, the surface aberrations 70 in FIG. 8 are circles and form a repeating pattern, while the surface aberrations 70 in FIG. 9 are hexagons and form a repeating pattern. Surface aberrations can have an area of, for example, about 0.005 cm$^2$ or more, about 0.01 cm$^2$ or more, or about 0.07 or more.

As can be seen in FIGS. 8 and 9, surface aberrations 70 have edges connecting their surface to the base substrate. These edges are formed during processing of the substrate to make the surface aberrations. During processes like vacuum forming, these edges maintain a similar thickness to that of the substrate before processing. This can help with stability of the substrate when it is processed into rolls. Some processes, like those used to form embossments and debossments, stretch the substrate resulting in edges to the embossments and debossments that are thinner than that of the substrate before processing which can cause issues with stability of the substrate when processing into rolls for transport.

A substrate can also comprise a feature. Substrate features can include, for example, design elements such as shapes and letters. Substrate features may reside, for example, within the land portions, the surface aberrations, or a combination thereof and may be located in plane, above plane, or below plane, or combinations thereof relative to either the land portion or surface aberration. Substrates with features out of plane with both the land and surface aberration portions are considered multiplanar substrates. Examples of features can be seen in FIGS. 8 (the "O"'s) and 9 (the stars).

Surface roughness can be added in the land area, in the portion of surface aberration areas that are closed, and/or on features, of substrates. Creating surface roughness results in a reduction of the gloss of the substrate surface which corresponds to a preferred consumer appearance. Gloss values can be, for example, less than about 3.5 or less than about 2.5.

A substrate can be multiplanar. For example, see FIGS. 8 and 9, where there is a first plane (P1) which is defined by land area on the surface aberrations 70 and a second plane (P2) which is defined by the land area of the base film. A second plane can be, for example, contiguous and repeating and generally non-porous. The second plane can generally be flat or can be flattened merely by placing the substrate on a table. The transition from first plane to second plane (70 in FIG. 8B) can be discrete as in FIGS. 8B and 9B which depict 90 degree angles or the transition can be stepped, tapered or occur at an angle less than about 90 degrees but greater than 0 degrees. A first plane can be, for example, discontinuous like in FIGS. 8 and 9. The first plane can be flat, raised, or even curved, so that it is not planar in the formal geometric sense, and is used to describe a base region from which protrusions can be raised and generally extends in an orthogonal direction to the protrusions and is the same plane as the original film from which the protrusions were raised. Surface aberrations which are similar (in the geometric sense) are considered to be in the same plane even if they are not connected to one another. Where the surface aberrations are dissimilar (for example, different heights from the plane of the original film), then they can create multiple planes.

Features 200, which can be continuous or discrete, can be added to the substrate and can represent additional planes or even add texture, for example patterns like starts, squares, logos can be embossed onto the substrate. Features 200 can also be at the same level of an existing plane, so can be considered part of an existing plane, and not an additional plane. A formed film is considered a planar substrate. A seal on a substrate is usually on such a similar level to an existing plane that it is considered as part of the existing plane and not creating an additional plane.

Some examples of suitable substrates are included below.

1. Formed Films

| Code | Material Description | Caliper and Basis Weight | Pore count/area; and diameter |
|---|---|---|---|
| F1 | Hydroapertured polyethylene film on 100 mesh screen, white (Tredegar, Inc.) | 166 microns, 24.5 gsm | 1,780/cm$^2$ — |
| F2 | Vacuum formed polyethylene film, white (SSRIS-CPM, Tredegar, Inc.) | 560 microns, 24.5 gsm | 115/cm$^2$ — |
| F3 | Vacuum formed polyethylene film, white 22 Hex (Tredegar, Inc.) | 560 microns, 24.4 gsm | 91/cm$^2$ ~500 micron |
| F4 | Vacuum formed polyethylene film, blue 11.2 Hex (Tredegar, Inc.) | 935 microns, 29.4 gsm | 22.2/cm$^2$ 1.1 mm |
| F5 | Vacuum formed polyethylene film, green (Tredegar, Inc.) | 670 microns, 36.0 gsm | 49/cm$^2$ 0.9 mm |
| F6 | Vacuum formed polyethylene film, white (Tredegar, Inc.) | 33.5 gsm | 12.6/cm$^2$ 1 mm |
| F7 | Vacuum formed polyethylene film 40 Hex | 418 microns, 35.8 gsm | 285/cm$^2$ — |
| F8 | Vacuum formed polyethylene film 8.75 Hex | 950 microns, 37.4 gsm | |

2. Fibrous Nonwovens

| Code | Material Description | Basis Weight |
|---|---|---|
| N1 | Spunlaid hydroentangled 100% PP (Avgol Nonwovens, NC, USA) | 47 gsm |
| N2 | Carded, calendar bonded all bicomponent PP/PE fiber (Fiberweb Inc., TN, USA) | 32 gsm |
| N3 | Spunbond, overbonded 100% PP (Experimental nonwoven) | 37 gsm |
| N4 | Carded, through air bonded 30/30/40 PP/Bicomponent PP-PE/Rayon (calendar patterned) | 62 gsm |

3. Fibrous Nonwoven Battings

| Code | Material Description | Caliper; and Basis Weight |
|---|---|---|
| B1 | Quilter's Fusible batting, low loft all polyester (Fairfield Processing, Danbury, CT, USA) | 2.50 mm, 160 gsm |
| B2 | Quilter's Fusible batting, low loft all polyester, ½ thickness (peeled) | 1.21 mm, 80 gsm |
| B3 | PROEF 12-334 polyester-bicomponent fiber blend batting (Libeltex, Belgium) | 1.54 mm, 100 gsm |
| B4 | PROEF 12-370 dual layer PET/copet bico and PP fibers; bulk layer with standard PET/coPET bico trilobal fibers (Libeltex, Belgium) | 0.60 mm, 55 gsm |
| B5 | Dry Web T30 SC batting, hollow PET + bico PET/PE fiber blend, through air bonded (Libeltex, Belgium) | 0.41 mm, 35 gsm |
| B6 | PROEF 12-372 batting, coarse polyester and PE/PET bico fibers (Libeltex, Belgium) | 0.55 mm, 50 gsm |
| B7 | Dry Web T23W batting, coarse polyester and bico fiber mix (Libeltex, Belgium) | 0.56 mm, 50 gsm |

4. Laminate Films

| Code | Material Description | Basis Weight |
|---|---|---|
| L1 | Formed film nonwoven laminate | 34 gsm |

5. Multiplanar Films

| Example | pattern | design or post processing | Thickness (micron) | Number of Pores per Sq. In. |
|---|---|---|---|---|
| Multi-planar 1 | 30 hex | Multiplanar with star shape feature and hexagonal land area, land area 7% | 1724 | 1035 (local) |
| Multi-planar 2 | 30 hex | Multiplanar with circular raised areas further with letter 'O' feature | 2640 | 1035 (local) |
| Multi-planar 3 | 30 hex | Biplanar with hexagonal pattern | 2514 | 1035 (local) |
| Multi-planar 4 | 30 hex | Biplanar | 1597 | 1035 (local) |
| Multi-planar 5 | | Biplanar with circular raised areas and 30% HDPE resin, 0.025 in. plane height, gloss of 3.2 | 1985 | 1840 (local) |
| Multi-planar 6 | | Biplanar with circular raised areas and 30% HDPE resin, 0.040 in. plane height, gloss of 2.9 | 2080 | 1840 (local) |
| Multi-planar 7 | | Biplanar with circular raised areas, 30% HDPE resin, 0.055 in. plane height, gloss of 2.5 | 3550 | 1840 (local) |
| Multi-planar 8 | | Biplanar with circular raised areas, 30% land area | 2012 | 1840 (local) |
| Multi-planar 9 | | Biplanar with circular raised areas, 44% land area | 2421 | 1840 (local) |

Caliper: ASTM D645;
gsm = grams per square meter
Air Permeability: ASTM D737

Methods of Use

Also included herein are methods directed to preserving personal care compositions. These can include methods for preserving, for example, personal cleansing compositions in an open system, where the method comprises including in the composition a first preservative with a log water solubility of less than 0 to about −5.0; wherein the composition has a consumption rate of 1.0 to about 10 g/use, a water activity of about 0.90 or more after 2 simulated uses, and a bacteria count of about 5000 or less when measured in accordance with the Microbial Content Method.

An additional method can be directed to, for example, preserving a multi-use personal cleansing article comprising a composition and a substrate, in an open system, comprising: including in the composition a first preservative with a log water solubility of less than 0 to about −5.0; wherein the composition has a consumption rate of 1.0 to about 10 g/use and a water activity of about 0.90 or more after 2 simulated uses.

Another method can be directed to, for example, preserving a high water activity composition in an open system, comprising: formulating the composition with a first preservative comprising a metal pyrithione, an organic acid, a glycol, or a combination thereof and a second preservative comprising sodium benzoate, methylchloroisothiazolinone, or a combination thereof; wherein the composition further comprises a fine, fiber, or filament comprising cellulose; and a surfactant; wherein the article has a consumption rate of 1.0 to about 10 g/use and the composition has a water activity of about 0.90 or more after 2 simulated uses.

The methods herein can include any of the subject matter described above like the compositional components and properties, the substrate components and properties, and the article components and properties, for example.

Examples

The following examples further describe and demonstrate compositions and articles within the scope of the present invention. In the following examples, all ingredients are listed at an active level. The examples are given solely for the purpose of illustration and are not to be construed as limitations of the personal care article or components thereof such as the composition or substrate, as many variations thereof are possible without departing from the spirit and scope disclosed herein. Substrate 1 represents the interior substrate in direct contact with the cleansing composition. Substrates 2 and 3 represent the exterior substrates in direct contact with the surface to be cleaned.

Comparative examples 1, 4, and 5, and Inventive examples 1-7, were prepared in the following manner. Liquid components (when included; zinc pyrithione, cocoamidylpropyl betaine, sodium trideceth sulfate, sodium laureth-1-sulfate, glycerin and a polyvinyl alcohol solution (prepared by dissolving polyvinyl alcohol in water)) were combined with water and preservatives (when included: citric acid) in a vessel and mixed with an overhead impeller mixing blade until homogeneous. Sodium cocoylisethionate, cocoamide monoethanolamine, cellulose fibers, and fragrance were combined in a speed mixing container and dry blended, mixing 30 seconds at 500 rpm in a speed mixer. The liquid solution was added to the dry components and the composition was mixed at 2000 rpm in speed mixer or until visually homogeneous. The resulting composition was then transferred to a lab scale 3 roll mill and passed through the mill 2 times. The resulting milled composition was then cut to the desired length/weight and sealed within the substrates.

| | Comparative Example 1 | Comparative Example 4 | Comparative Example 5 |
|---|---|---|---|
| Sodium Cocoylisethionate | | 19.30 | 19.30 |
| Cocoamide Monoethanolamine | | 4.70 | 4.70 |
| Cocoamidylpropyl betaine | 8.25 | | |
| Sodium Benzoate | | | 0.25 |
| EDTA | | | 0.10 |
| Citric Acid | 0.35 | 0.40 | 0.40 |
| Sodium Trideceth Sulfate | 28.93 | 10.00 | 10.00 |
| Polyvinyl Alcohol | | 1.50 | 1.50 |
| Perfume | 1.5 | 2.00 | 2.00 |
| Kathon ™ | | | 0.03 |
| Cellulose | 19.00 | 28.30 | 28.30 |
| Zinc Pyrithione | | | |
| Water | 41.97 | 33.80 | 33.42 |
| Substrate 1 | Formed Film F7 | Formed Film F7 | Formed Film F7 |
| Substrate 2 | Laminate L1 | Laminate L1 | Laminate L1 |
| Substrate 3 | Multi-planar 2 | Multi-planar 2 | Multi-planar 2 |
| Consumption rate of article | Approx. 3.0-6.0 | 4.7 | 4.7 |

| | Inventive Example 1 | Inventive Example 2 | Inventive Example 3 | Inventive Example 4 |
|---|---|---|---|---|
| Sodium cocoylisethionate | 18.90% | 21.00% | — | 19.30% |
| Cocoamide monoethanolamine | 11.70% | 13.00% | — | 4.70% |
| Sodium laureth-1-sulfate | — | — | 25.00% | — |
| Sodium Trideceth Sulfate | — | — | — | 10.00% |
| Cocoamidylpropyl betaine | 10.00% | 11.00% | 2.14% | — |
| Glycerin | 10.00% | — | — | — |
| Cellulose | 19% | 20% | — | 28.30% |
| Polyvinyl Alcohol | — | — | 14.43% | 1.50% |
| Sodium Benzoate | 0.25% | 0.25% | 0.25% | 0.25% |
| FPS ZPT | 0.40% | — | — | 0.40% |
| Salicylic acid | — | 0.50% | — | — |
| Ethylenediaminetetra acetic acid | — | — | 0.10% | — |
| Citric Acid | 0.25% | 0.50% | 0.25% | — |
| Kathon ™ | — | — | 0.03% | — |
| Fragrance | 2.00% | 2.00% | 2.00% | 2.00% |
| water | 27.50% | 31.75% | 55.80% | 33.55% |
| Substrate 1 | Formed Film F7 | Formed Film F7 | Formed Film F7 | Formed Film F7 |
| Substrate 2 | laminate L1 | laminate L1 | laminate L1 | laminate L1 |
| Substrate 3 | Multi-planar 2 | Multi-planar 2 | Multi-planar 2 | Multi-planar 2 |
| Consumption Rate (g/use) | 2.4 | 2.4 | 0.85 | 4.8 |
| Composition pH range | 5.0-7.0 | 3.5-5.0 | 5.0-7.0 | 5.0-7.0 |
| Composition water activity before use | 0.78 | 0.87 | 0.98 | approx. 0.95 |

| | Inventive Example 5 | Inventive Example 6 | Inventive Example 7 |
|---|---|---|---|
| Sodium cocoylisethionate | — | — | 19.00% |
| Cocoamide monoethanolamine | — | — | 12.00% |
| Sodium laureth-1-sulfate | — | — | — |
| Sodium Trideceth Sulfate | 28.93% | 28.93% | — |
| Cocoamidylpropyl betaine | 8.25% | 8.25% | — |
| Glycerin | — | — | 7.50% |
| Cellulose | 19.00% | 19.00% | 21.00% |

| | -continued | | |
|---|---|---|---|
| Polyvinyl Alcohol | — | — | — |
| Sodium Benzoate | 0.25% | 0.25% | 0.25% |
| FPS ZPT | 0.50% | — | — |
| Salicylic acid | — | 0.20% | — |
| Ethylenediaminetetra | — | — | — |
| acetic acid | | | |
| Geogard ECT (salicylic acid, sorbic acid, benzyl alcohol, and glycerin) | — | — | 1.00% |
| Citric Acid | 0.35% | — | 0.25% |
| Kathon ™ | — | — | — |
| Fragrance | 1.50% | 1.50% | 3.00% |
| water | 41.22% | 41.87% | 36.00% |
| Substrate 1 | Formed Film F7 | Formed Film F7 | Formed Film F7 |
| Substrate 2 | laminate L1 | laminate L1 | laminate L1 |
| Substrate 3 | Multi-planar 2 | Multi-planar 2 | Multi-planar 2 |
| Consumption Rate (g/use) | Approx. 3.0-6.0 | Approx. 3.0-6.0 | Approx. 3.0-6.0 |
| Composition pH range | 5.0-7.0 | 3.5-5.0 | 3.5-6.5 |
| Composition water activity before use | Approx. 0.95 | Approx. 0.95 | Approx. 0.88 |

Inventive Examples D1-D5 are made in the following manner. Cocamidopropyl betaine was combined with preservatives in a tank equipped with an impeller mixing blade. Sodium cocoylisethionate, cocoamide monoethanolamine, cellulose fibers, zinc pyrithione (when included), and fragrance were combined in an amalgamator typically employed in bar soap making. The cocamidopropyl betaine/preservative solution was added into the amalgamator and the composition was mixed until visually homogeneous. The resulting amalgamated composition was then transferred to a conventional bar soap 3 roll mill and passed through the mill 2 times. The resulting milled composition was then passed through a conventional bar soap plodder and cut to the desired length.

Comparative example C1 can be prepared by combining each of the ingredients listed in the table below and speed mixing the mixture at 2,000 rpm for 30 seconds to generate a homogeneous composition.

Approximately, 50 g of each composition was sealed within substrates, with the interior substrate being example substrate F7, one of the contact substrates being example substrate L1 and the other contact substrate being Multiplanar 2.

| Inventive Example Number | Hygroscopic Material Example | Sodium Cocoyl Isethionate (raw material wt %-85% active) | Cocoamido-propyl betaine | Cocoamide monoethanolamine (raw material wt %-85% active) | High Solubility Preservative | ZPT | Fragrance | Hygroscopic Material % | Water |
|---|---|---|---|---|---|---|---|---|---|
| Example D1 | Example HG4 | 21.18 | 9.45 | 13.11 | 0.34 | 0.34 | 3.43 | 17.14 | 36.63 |
| Example D2 | Example HG4 | 51.18 | 5.51 | 27.06 | 0.20 | 0.20 | 2.00 | 10.00 | 7.71 |
| Example D3 | Example HG4 | 42.35 | 7.35 | 23.14 | 0.27 | 0.27 | 2.67 | 13.33 | 13.83 |
| Example D4 | Example HG4 | 24.71 | 11.03 | 15.29 | 0.40 | 0.40 | 4.00 | 20.00 | 26.07 |
| Example D5 | Example HG4 | 21.62 | 9.65 | 13.38 | 0.35 | 0.35 | 3.50 | 30.00 | 22.81 |

| Comparative Example Number | Hygroscopic Material | Sodium Laureth Sulfate | Cocoamido-propyl betaine | Glycerin | Preservatives | Laponite Clay | Fragrance | Water |
|---|---|---|---|---|---|---|---|---|
| Example C1 | Laponite Clay | 18.0% | 2.4% | 21.7% | 0.6% | 43.5% | 0.9% | 12.9% |

The article compliance and composition rheology values of the above example compositions are:

| Composition | Article Compliance (kg/mm) | | |
|---|---|---|---|
| Example Number | Prior To Use | 30 min After Use | 50.5 Hrs After Use |
| Example D1 | 0.20 | 0.17 | 0.33 |
| Example D2 | 1.16 | 0.61 | 1.04 |
| Example D3 | 0.52 | 0.32 | 0.61 |
| Example D4 | 0.22 | 0.18 | 0.34 |
| Example D5 | 0.49 | 0.45 | 0.57 |

Test Methods a) Compliance Test

To measure the compliance of an article or composition prior to use, use a Texture Analyzer TA-XT2i (Texture Technologies Corp, NY, USA) equipped with at least a 5 kg load cell and a 0.75 inch ball probe at ambient conditions. Start the test with the probe above but not in contact with the article or composition and use a 2 gram trigger force to commence data collection for both force and distance (i.e., the zero depth point begins at 2 gram-force). Measure a compressive force (kg) at a compression rate of 1 mm/sec over a depth of 5 mm, ensuring that the personal care article or composition form a flat surface over contact area with the ball probe, near the center of the article or composition. Repeat measurements as needed (e.g., at least 3 times) to obtain a representative average value. To determine the compliance of the article or composition divide the maximum observed force (kg) by the maximum compression depth (5 mm) When using a 5 kg load cell some samples may exceed capacity, in this case the maximum compression depth will be less than the set depth of 5 mm, specified in the procedure. Compliance of the article includes a measured force contribution of both the composition and substrate components. If thick or lofty substrates are used such that the probe does not substantially engage a composition component, or if the composition is distributed heterogeneously, the test is performed in a region and to a depth such that the composition component is a substantial contributor to the measured compliance. For example, if thick or lofty substrates are used in an article, the trigger force can be increased until the zero point is within at least about 0.5 mm of the composition.

To measure compliance after a simulated bath/shower use a rotary tumbler (Lortone, Inc., Seattle, Wash., USA model 33B or equivalent) with 4 in. diameter by 4 in. deep cylindrical rubber housing having 825 cc internal volume. The housing revolves on the tumbler at 43 rpm. Obtain a supply of water at about 7.5 grains water hardness and conductivity between 100 to not more than 400 microSemens per centimeter (μS/cm) and heat in a reservoir beaker to 45° C. Maintain the water reservoir at the target temperature within 1 degree. Add 200.0 gm of water from the reservoir to the housing. Weigh an article or composition to obtain the initial weight, and add the article or composition to the housing. Seal the housing with its accompanying watertight lid and place the sealed housing onto the rotary tumbler for 3 minutes. Remove the housing, remove the housing lid, and retrieve the article or composition.

Hang the article or composition to dry under controlled temperature (20-25° C.) and relative humidity (50-60%) with no direct air circulation applied to articles. Take compliance measurements as a function of time. The first time point after simulated use should be no sooner than 5 min after the product has been removed from the rotary tumbler and hung to dry. The final time point can be taken at any point as desired or instructed. For example, the final point can be taken after 15 minutes of drying after one use; after 20 minutes of drying after one use; after 30 minutes of drying after one use; after 60 minutes of drying after one use; after 3 hours of drying after one use; after 5 hours of drying after one use; after 12 hours of drying after one use; after 25 hours of drying after one use; or after 48 hours of drying after one use. When measuring compliance after multiple simulated uses, dry the composition or article for 5 minutes between each simulated use and after the final simulated use, unless the drying time is otherwise specified. For example, to measure compliance after 2 simulated uses, the composition would be put through a simulated use cycle, dried for 5 minutes, put through the second simulated use cycle, dried for 5 minutes and then the compliance measured.

b) Dissolution Rate Test

Obtain a straight walled glass beaker having an inside diameter (i.d.) of 63 mm and an inside height of 87 mm, (e.g., Pyrex 250 mL (No. 1000) which are widely available). Pour 150 grams of distilled water at ambient temperature (75° F.) into the beaker and add a Teflon® coated magnetic stir bar to the beaker. (Note: The stir bar can be nominally 1.5 inches long×5/16 inches diameter, octagonally-shaped as viewed from the end, and can have a 1/16 in. wide molded pivot ring around its center where the diameter can be about 0.35 in.) Examples of a suitable stir bar can include Spinbar® magnetic stir bars available from Sigma Aldrich Corp. worldwide including Milwaukee, Wis., USA and at www.sigmaaldrich.com.

Measure and record the water conductivity of the water using a conductivity meter (e.g., a Mettler-Toledo Seven-Multi meter with InLab740 probe). (Note: The conductivity of the water should be about 2 microSemens/cm (uS/cm) or less to indicate a low level of dissolved solids present.) Remove the conductivity probe from the water and place the beaker onto a digitally controlled laboratory stirrer, for example Ika® Werke RET Control-visc available (e.g., from DivTech Equipment Co, Cincinnati, Ohio, USA). Center the beaker on the stirrer and turn the stirrer on to obtain a constant rotation speed of 500 rpm to establish a vortex in the water which measures about 3 cm depth from highest point of water at the beaker edge to lowest point of air at the vortex center. Observe the vortex from above to ensure the beaker is centered and that the magnetic stir bar is centered in the vortex. Weigh 1.0 grams of a composition pressed or formed together as a single unit and add it to the water near the beaker edge but not touching the beaker edge. Begin a timer and allow the water with composition to stir for 1 minute.

Turn off the stirrer. Insert the conductivity probe into the water in a location away from any undissolved material. Allow a measurement to stabilize for a few seconds and record conductivity. Turn the stirrer back on. Restart the timer as the digital readout passes 250 rpm. After an additional 1 minute has elapsed, turn off the stirrer and measure and record conductivity in the same manner as above. Turn the stirrer back on. Restart the timer as the digital readout passes 250 rpm. Repeat the process until a conductivity reading has been obtained every minute of stirring, for 5 minutes.

After taking a 5 minute conductivity reading, cap the beaker with a suitable watertight cover (e.g., plastic wrap). Shake the beaker vigorously for about 1 minute to dissolve remaining solids, using a vortex type agitator and/or mild heating in addition if necessary until all soluble components are observed dissolved by visible inspection. Cool the solution to less than 80° F. prior to the final measurement. Uncap the beaker, measure conductivity and record the value as a final conductivity.

Calculate the fractional dissolution (f) at each time point by the equation: f=(conductivity−water conductivity)/(final conductivity−water conductivity)

Calculate the dissolution half-life by fitting the fractional dissolution time series (6 points from 0 to 5 minutes) to a second order polynomial and calculate an interpolated or extrapolated result for a time at which a composition is half dissolved (i.e., f=0.5).

Dissolution half-life can be a measure of the propensity of a composition to resist solubilization by water. Bars of soap, for example, can have a dissolution half-life of 21.1 minutes (Ivory®™ Soap), exhibiting longevity and low consumption rate during use without a need for substrates as barriers to permeability. Liquid body wash can have a dissolution half-life of less than ½ minute and can be unsuitable as a composition for such articles.

c) Consumption Test

To measure the Consumption Rate of a personal care article or composition per simulated use as noted in this test method (not the Compliance test method), use a rotary tumbler (Lortone, Inc., Seattle, Wash., USA model 33B or equivalent) with a 4 in. diameter by 4 in. deep cylindrical rubber housing having 825 cc internal volume. The housing revolves on the tumbler at 43 rpm. Obtain a supply of tap water at about 7.5 grains water hardness and conductivity between 100 to not more than 400 microSemens per centimeter (μS/cm) and heat in a reservoir beaker to 45° C. Maintain the water supply at the target temperature within 1 degree for the test duration. Add 200.0 g water from the reservoir to the housing. Weigh an article or composition to obtain the initial weight, and add the article or composition to the housing. Seal the housing with its accompanying watertight lid and place the sealed housing onto the rotary tumbler for exactly 3 minutes. Remove the housing, remove the housing lid, and retrieve the article or composition. Stir the remaining water in the housing for a few seconds and measure its conductivity and temperature using a Mettler Toledo Seven multimeter with InLab 740 probe or equivalent. Dry the article or composition surface by pressing, not rubbing, using paper towels with light hand pressure for about 30 seconds, until it is dry to the touch and transfers no more visible water to a dry paper towel using the same pressure at any point on its surface or edges. If the article or composition transfers partially dissolved or dissolving components in addition to liquid water (e.g., if a composition is a conventional bar soap it may transfer paste-like material), the transferred components are to be removed and the article or composition is considered dry when visible transfer is no longer evident. Weigh the article or composition. Repeat this with the same article or composition five times. Subtract the weight after the fifth cycle from the weight after the second cycle and divide by 3 to obtain the consumption rate reported in units g/use.

d) Microbial Susceptibility Method

Each composition is removed aseptically from inside the substrate(s) (if necessary). Then four equal size aliquots (ex. weighing ~15 g) of the composition are placed in separate sterile Whirlpak bags. The compositions are flattened to increase surface contact area and inoculated on one side with 0.25 ml of $10^6$ cfu/g of either an enteric pool or a *Pseudomonas* pool. The enteric pool consists of environmental isolates *Citrobacter freundii, Enterobacter cloacae, E. gergoviae, Serratia marcescens* and two isolates of *Klebsiella pneumoniae* along with two American Type Culture Collection (ATCC) strains *Candida albicans* (10231) and *Staphylococcus aureus* (6538). The *Pseudomonas* pool contains environmental isolates *Burkholderia cepacia, Pseudomonas aeruginosa, P. fluorescens* and a *Pseudomonas* spp. plus an ATCC strain *P. aeruginosa* (15442). The inoculum is spread evenly over the surface of the composition. After inoculation, each aliquot is stored at 20-25° C. until sampling is conducted on days 7 and 14.

For the two sampling time points, 90 ml of sterile modified letheen broth with 1.5% Tween 80 and 1% Lecithin (MLBTL) is added to each aliquot and stomached for two minutes at 260 rpm using a Seward Stomacher 400 Circulator. Then serial dilutions are performed ($10^{-2}$-$10^{-6}$) in MLBTL diluent, and 1 ml of each dilution is plated onto 50 ml of modified letheen agar with 1.5% Tween 80 (MLAT) followed by a 72 hr incubation at 30-35° C. Finally, microbial colony forming units are counted manually and log reduction is calculated for each time point.

e) Microbial Content Method

The composition is removed aseptically from the substrates (if needed). 1:10 serial dilutions are performed in MLBTL. The dilution bottle is shaken to evenly disperse the sample. 0.5 ml aliquots from each dilution are spread onto two MLAT plates with one plate incubated at 25° C. and the other plate at 32° C., each for 72 hours. Microbial colony forming units are counted manually to determine cfu/g on each plate. All plates should meet the target set. For example, if the target is set at a bacteria count of about 5000 or less, then all plates should be below that threshold.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-use personal cleansing article, comprising:
   a) from about 40% to about 99.6%, by weight of the article, of a soft solid cleansing composition, comprising;
      i) from about 20% to about 80%, by weight of the composition, of a surfactant comprising cocoamide monoethanolamine, cocoamidopropyl betaine, decyl glucoside, lauryl glucoside, an alkyl sulfate, an alkyl sulfonate, or a combination thereof;
      ii) from about 3% to about 40%, by weight of the composition, of a fine, fiber, or filament, comprising cellulose;
      iii) a solvent;
      iv) a first preservative comprising an organic acid, citric acid, salicylic acid, sorbic acid, zinc pyrithione, or a combination thereof; and
      v) a second preservative comprising methylisothiazolinone, sodium benzoate, or a combination thereof; and
   b) a water insoluble substrate at least partially surrounding the composition;
      wherein the article has a compliance value of about 0.1 kg/mm to about 1.5 kg/mm after two simulated uses and a consumption rate of 1.0 to about 10.0 g/use; and the composition has a water activity of about 0.90 or more after two simulated uses.

2. The multi-use personal cleansing article of claim 1, wherein the water insoluble substrate comprises a multiplanar film.

3. The multi-use personal cleansing article of claim 1, wherein the water insoluble substrate comprises a multiplanar vacuum formed film.

4. The multi-use personal cleansing article of claim 1, wherein the first preservative comprising zinc pyrithione.

5. The multi-use personal cleansing article of claim 1, wherein the composition has a compliance value of about 0.10 kg/mm to about 0.3 kg/mm before a simulated use.

6. The multi-use personal cleansing article of claim 1, wherein the composition comprises the filament which comprises fibers and fines and the fibers have an aspect ratio of about 9 to about 1,000.

7. The multi-use personal cleansing article of claim 1, wherein the composition has a compliance value of 0.01 mm/kg to about 1.5 mm/kg after 48 hours of drying after one simulated use.

8. The multi-use personal cleansing article of claim 1, wherein the water insoluble substrate surrounds the composition.

9. The multi-use personal cleansing article of claim 1, wherein the substrate is water penetrable.

10. The multi-use personal cleansing article of claim 9, wherein a second substrate is adjacent to the water insoluble substrate.

11. The multi-use personal cleansing article of claim 10, wherein the second substrate is water penetrable.

12. The multi-use personal cleansing article of claim 9, wherein the cellulose derives from a plant.

13. The multi-use personal cleansing article of claim 12, wherein the composition comprises from about 15% to about 25%, by weight of the composition, of the cellulose.

\* \* \* \* \*